(12) United States Patent
Popoff et al.

(10) Patent No.: US 6,812,002 B2
(45) Date of Patent: Nov. 2, 2004

(54) OSTEOACTIVIN PROTEIN AND NUCLEIC ACIDS ENCODING THE SAME, COMPOSITIONS AND METHODS OF STIMULATING BONE DIFFERENTIATION

(75) Inventors: Steven N. Popoff, Warrington, PA (US); Fayez F. Safadi, Philadelphia, PA (US); Thomas A. Owen, East Lyme, CT (US); Steven L. Smock, Baltic, CT (US)

(73) Assignees: Pfizer Inc., New York, NY (US); Temple Univeristy, Philadelphia, PA (US)

( * ) Notice: Subject to any disclaimer, the term of this patent is extended or adjusted under 35 U.S.C. 154(b) by 0 days.

(21) Appl. No.: 09/943,075

(22) Filed: Aug. 30, 2001

(65) Prior Publication Data

US 2002/0151486 A1 Oct. 17, 2002

Related U.S. Application Data

(60) Provisional application No. 60/229,006, filed on Aug. 30, 2000.

(51) Int. Cl.[7] .......................... C12N 15/19; C12N 5/10; C12N 15/85
(52) U.S. Cl. .................... 435/69.1; 435/320.1; 435/325; 435/455; 536/23.1; 536/23.5
(58) Field of Search ............................ 435/69.1, 320.1, 435/325, 455; 536/23.1, 23.5; 514/44

(56) References Cited

U.S. PATENT DOCUMENTS 6,242,419 B1 * 6/2001 Strachan et al. ............... 514/12

FOREIGN PATENT DOCUMENTS

WO    WO 97/44460 A1 * 11/1997

OTHER PUBLICATIONS

Ngo et al., "Computational complexity, protein structure prediction, and the Levinthal paradox," in The Protein Folding Problem and Tertiary Structure Prediction, Merz et al. (eds.), Birkhauser Boston: Boston, MA, pp. 433 and 492–495, 1994.*

Rudinger, J., "Characteristics of the amino acids as components of a peptide hormone sequence," (in Peptide Hormones, Parsons (ed.), University Park Press: Baltimore, MD, pp. 1–7, 1976.*

Anderson et al., "Mutations in genes encoding melanosomal proteins cause pigmentary glaucoma in DBA/2J mice," Nature Genetics 30: 81–85, Jan. 2002.*

Orkin et al., Report and recommendations of the panel to assess the NIH investment in research on gene therapy, issued by the U.S. National Institutes of Health, Bethseda, MD, Dec. 7, 1995.*

Verma et al., "Gene therapy—promises, problems and prospects," Nature 389: 239–242, Sep. 18, 1997.*

Rosenberg et al., "Gene Therapist, heal thyself," Science 287 : 1751, Mar. 10, 2000.*

Bachner, D., "Mus musculus mRNA for putative transmembrane glycoprotein (NMB gene)," GenBank Acc. No. AJ251685, US National Library of Medicine, Bethseda, MD, Jan. 7, 2000, accessed by the PTO Apr. 7, 2003.*

Xu, et al. (1999) "Cloning and Characterization of a Novel cDNA Highly Expressed in Osteopetrotic Bone," *Journal of Bone and Mineral Research*. vol. 14, Suppl 1, pp. S469.

GenBank Sequence, Accession No. AF184983 and GI6090938 (1999).

Weterman et al. (1995) "*nmb*, A Novel Gene, Is Expressed in Low–Metastic Human Melanoma Cell Lines And Exenografts," *Int. J. Cancer*: 60, 73–81.

* cited by examiner

Primary Examiner—Scott D. Priebe
(74) Attorney, Agent, or Firm—Clark & Elbing LLP

(57) ABSTRACT

The invention provides osteoactivin proteins and nucleic acid molecules that encode the same, as well as biologically functional expression vectors containing nucleic acid molecules encoding osteoactivin proteins, and antibodies specific for osteoactivin proteins. The invention also provides therapeutic and diagnostic compositions and methods for utilizing the proteins, antibodies, nucleic acids, and vectors of the invention, for example, to modulate bone formation.

13 Claims, 18 Drawing Sheets

FIG. 1A

| FIG. 1A-1 |
| FIG. 1A-2 |

| EXON | BAC Start | BAC Stop | cDNA Start | cDNA Stop | Exon Length |
|------|-----------|----------|------------|-----------|-------------|
| 1 | 83294 | 83455 | 1 | 162 | 162 |
| 2 | 89834 | 89986 | 163 | 314 | 152 |
| 3 | 90696 | 90839 | 315 | 458 | 144 |
| 4 | 93419 | 93594 | 459 | 634 | 176 |
| 5 | 96509 | 96665 | 635 | 791 | 157 |
| 6 | 96983 | 97300 | 792 | 1109 | 318 |
| 7 | 103044 | 103142 | 1110 | 1208 | 99 |
| 8 | 104413 | 104515 | 1209 | 1311 | 103 |
| 9 | 106494 | 106702 | 1312 | 1520 | 209 |
| 10 | 110048 | 110141 | 1521 | 1614 | 94 |
| 11 | 110592 | 111633 | 1615 | 2656 | 1042 | poly A signal is position 111614-111619 translation start (ATG) is:
cDNA: 92
Gene: 83385

| FIG. 2A-1 |
| FIG. 2A-2 |
| FIG. 2A-3 |
| FIG. 2A-4 |
| FIG. 2A-5 |

FIG. 2A

| | | | | | | |
|---|---|---|---|---|---|---|
| rat   | ATGGAAAGTC | TCTGCGGGGT | CCTGGTATTT | CTGCTGCTGG | CTGCAGGACT | GCCGCTCCAG | GCGGCCAAGC GGTTC 75 |
| mouse | ATGGAAAGTC | TCTGCGGGGT | CCTGGGATTT | CTGCTGCTGG | CTGCAGGACT | GCCTCTCCAG | GCTGCCAAGC GATTT 75 |
| human | ATGGAAAGTC | TCTACTATTT | CCTGGGATTT | CTGCTCCTGG | CTGCAAGATT | GCCACTTGAT | GCCCCCAAAC GATTT 75 |
| rat   | CGTGATGTGC | TGGGCCATGA | GCAGTATCCG | GATCACATGA | GGGAGAACAA | CCAATTACGT | GGCTGGTCTT CAGAT 150 |
| mouse | CGTGATGTGC | TGGGCCATGA | ACAGTATCCC | GATCACATGA | GAGAGCACAA | CCAATTACGT | GGCTGGTCTT CGGAT 150 |
| human | CATGATGTGC | TGGCAATGA  | AAGACCTTCT | GCTTACATGA | GGGAGCACAA | TCAATTAAAT | GGCTGGTCTT CTGAT 150 |
| rat   | GAAAATGAAT | GGGATGAACA | GCTGTATCCA | GTGTGGAGGA | GGGAGAGGG  | CAGATGGAAG | GACTCCTGGG AAGGA 225 |
| mouse | GAAAATGAAT | GGGATGAACA | CCTGTATCCA | GTGTGGAGGA | GGGGAGACGG | CAGGTGGAAG | GACTCCTGGG AAGGA 225 |
| human | GAAATGACT  | GGAATGAAAA | ACTCTACCCA | GTGTGGAAGC | GGGGAGACAT | GAGGTGGAAA | AACTCCTGGA AGGGA 225 |
| rat   | GGCCGTGTGC | AGGCAGCCCT | AACCAGTGAT | TCACCGGCCT | TGGTTGGGTTC | CAATATCACC | TTCGTAGTGA ACCTG 300 |
| mouse | GGCCGTGTGC | AGGCAGTCCT | GACCAGTGAC | TCACCGGGCTC | TGGTGGGTTC | CAATATCACT | TTTGTGGTGA ACCTG 300 |
| human | GGCCGTGTGC | AGGCCGGTCCT | GACCAGTGAC | TCACCAGCCC | TCGTGGGCTC | AAATATAACA | TTTGCGGTGA ACCTG 300 |

FIG. 2A-1

```
rat    GTGTTCCCCA GATGCCAGAA GGAAGATGCC AACGGCAATA TCGTCTATGA GAGGAACTGC AGAAGTGATT TGGAG    375
mouse  GTGTTCCCCA GATGCCAGAA GGAAGATGCT AATGGCAATA TCGTCTATGA GAAGAACTGC AGGAATGATT TGGGA    375
human  ATATTCCCTA GATGCCAAAA GGAAGATGCC AATGGCAACA TAGTCTATGA GAAGAACTGC AGAAATGAGG CTGGT    375 rat    CTGGCTTCTG ACCCGTATGT CTACAACTGG ACCACAGGGG CAGACGATGA GGACTGGGAA GACAACACCA GCCAA    450
mouse  CTGACATCTG ACCTGCATGT CTACAACTGG ACTGCAGGGG CAGATGATGG TGACTGGGAA GATGGCACCA GCCGA    450
human  TTATCTGCTG ATCCATATGT TTACAACTGG ACAGCATGGT CAGAGGACAG TGACGGGGAA AATGGCACCG GCCAA    450 rat    GGCCAGCACC TCAGGTTCCC CGACGGGAAG CCCTTCCCTC GCCCCCACGG ACGGAAGAAA TGGAACTTCG TCTAC    525
mouse  AGCCAGCATC TCAGGTTCCC GGACACAGAG CCCTTCCCTC GCCCCCCATGG ATGGAAGAAA TGGAGCTTTG TCTAC    525
human  AGCCATCATA AGTCTTCCC TGTGGGAAA CCTTTTCCTC ACCACCCCGG ATGGAGAAGA TGGAATTTCA TCTAC    525 rat    GTCTTCCACA CACTTGGTCA GTATTTCAA AAGCTGGGTC AGTGTTCAGC ACGAGTTTCT ATAAACACAG TCAAC    600
mouse  GTCTTCCACA CACTTGGGCCA GTATTTCCAA AAACTGGGTC GGTGTTCAGC ACGGGTTTCT ATAAACACAG TCAAC    600
human  GTCTTCCACA CACTTGGTCA GTATTTCCAG AAATTGGGAC GATGTTCAGT GAGAGTTTCT GTGAACACAG CCAAT    600 rat    TTGACAGTTG GCCCTCAGGT CATGGAAGTG ATTGTCTTTC GAAGACACGG CCGGGCATAC ATTCCCATCT CCAAA    675
mouse  TTGACACTG GCCCTCAGGT CATGGAAGTG ACTGTCTTTC GAAGATACGG CCGGGCATAC ATTCCCATCT CGAAG    675
human  GTGACACTTG GGCCTCAACT CATGGAAGTG ACTGTCTACA GAAGACATGG ACGGGCATAT GTTCCCATCG CACAA    675
```

FIG. 2A-2

| | | | | | |
|---|---|---|---|---|---|
| rat | GTGAAGACG | TGTATGTGAT | AACAGATCAG | ATCCCTATAT | TCGTGACCAT | GTACCAGAAG | AATGACCGGA | ACTCG | 750 |
| mouse | GTGAAAGATG | TGTATGTGAT | AACAGATCAG | ATCCCTGTAT | TCGTGACCAT | GTCCCAGAAG | AATGACAGGA | ACTTG | 750 |
| human | GTGAAAGATG | TGTACGTGGT | AACAGATCAG | ATTCCTGTGT | TTGTGACTAT | GTTCCAGAAG | AACGATCGAA | ATTCA | 750 |
| | | | | | | | | | |
| rat | TCTGATGAAA | CCTTCCTCAG | AGACCTCCCC | ATTTTCTTCG | ATGTCCTCAT | TCACGATCCC | AGTCATTTCC | TCAAC | 825 |
| mouse | TCTGATGAGA | TCTTCCTCAG | AGACCTCCCC | ATCGTCTTCG | ATGTCCTCAT | TCATGATCCC | AGCCACTTCC | TCAAC | 825 |
| human | TCCGACGAAA | CCTTCCTCAA | AGATCTCCCA | ATTATGTTTG | ATGTCCTGAT | TCATGATCCT | AGCCACTTCC | TCAAT | 825 |
| | | | | | | | | | |
| rat | TACTCTGCCA | TTTCCTACAA | GTGGAACTTT | GGGGACAACA | CTGGCCTGTT | TGTCTCCAAC | AATCACACTT | TGAAT | 900 |
| mouse | GACTCTGCCA | TTTCCTACAA | GTGGAACTTT | GGGGACAAACA | CTGGCCTGTT | TGTCTCCAAC | AATCACACTT | TGAAT | 900 |
| human | TATTCTACCA | TTAACTACAA | AGATCTCCAA | GTGGAGCTTC | CTGGCCTGTT | TGTTTCCACC | AATCATACTG | TGAAT | 900 |
| | | | | | | | | | |
| rat | CACACGTATG | TGCTCAATGG | AACCTTCAAC | TTTAACCTCA | CCGTGCAAAC | TGCAGTGCCG | GG------ | -ACCA | 966 |
| mouse | CACACTTATG | TGCTCAATGG | AACCTTCAAC | CTTAACCTCA | CCGTGCAAAC | TGCAGTGCCC | GG------ | -GCCA | 966 |
| human | CACACGTATG | TGCTCAATGG | AACCTTCAGC | CTTAACCTCA | CTGTGAAAGC | TGCAGCACCA | GGACCTGTC | CGCCA | 975 |
| | | | | | | | | | |
| rat | -TGCC-CC-T | CACCCACACC | TTCGCCTTCT | CTCCTTC-- | ---GCCTGCA | TCTTCGCCTT | CA--- | | 1029 |
| mouse | -TGCC-C--T | --CCC---CC | TTCGCCTTCG | ACTCCGCCTT | CACCTTCAAC | CCTTCGCCCTTA | CCCTTCGCCCT | CACCT | 1032 |
| human | CCGCCACCAC | CACCCAGACC | TTC------- | ---------- | -----AA | ------A | ---- | -ACC- | 1004 |

FIG. 2A-3

| | | | | | |
|---|---|---|---|---|---|
| rat | ---CCCACAT | TATCAACACC | TAGTCCCTCT | TTAATGCCTA | CTGGCTACACA ATCCATGGAG CTGAGTGACA TTTCC | 1101
| mouse | TTGCCCACAT | TATCAACACC | TAGCCCCTCT | TTAATGCCTA | CTGGTTACAA ATCCATGGAG CTGAGTGACA TTTCC | 1107
| human | ---------- | ----CACC | ----CCTTCT | TTAGGACCTG | CTGGTGACAA CCCCCTGGAG CTGAGTAGGA TTCCT | 1059 rat     AATGAAAACT GCCGAATAAA CAGATAAGGT TACTTCAGAG CCACCATCAC AATTGTAGAT GGAATCCTAG AAGTC 1176
mouse   AATGAAAACT GCCGAATAAA CAGATAAGGC TACTTCAGAG CCACCATCAC AATTGTAGAG GGGATCCTGG AAGTC 1182
human   GATGAAAACT GCCAGATTAA CAGATAAGGC TACTTTCAAG CCACCATCAC AATTGTAGAG GGAATCTTAG AGGTT 1134 rat     AACATCATCC AGGTAGCAGA TGTCCCAATC CCCACACTGC AGCCTGACAA CTCACTGATG GACTTCATTG TGACC 1251
mouse   AGCATCATGC AGATAGCAGA TGTCCCCCATG CCCACACCGC AGCCTGCCAA CTCCCTGATG GACTTCACTG TGACC 1257
human   AACATCATCC AGATGACAGA CGTCCTGATG CCGGTGCCAT GGCCTGAAAG CTCCCTAATA GACTTTGTCG TGACC 1209 rat     TGCAAAGGGG CCACTCCCAC GGAAGCCTGT ACGATCATCT CTGACCCCAC CTGCCAGATC GCCCAGAACA GGGTG 1326
mouse   TGCAAAGGGG CCACCCCCAT GGAAGCCTGT ACGATCATCT CCGACCCCAC CTGCCAGATC GCCCAGAACC GGGTC 1332
human   TGCCAAGGGA GCATTCCCAC GGAGGTCTGT ACCATCATTT CTGACCCCAC CTGCGAGATC ACCCAGAACA CAGTC 1284 rat     TGCAGCCCGG TGGCTGTGGA TGAGCTGTGC CTCCTGTCCG TGAGGAGAGC CTTCAATGGG TCCGGCACGT ACTGT 1401
mouse   TGCAGCCCTG TGGCTGTGGA TGGGCTGTGC CTGCTGTCTG TGAGAGAGC CTTCAATGGG TCTGGCACCT ACTGT 1407
human   TGCAGCCCTG TGGATGTGGA TGAGATGTGT CTGCTGACTG TGAGACGAAC CTTCAATGGG TCTGGGACGT ACTGT 1359

FIG. 2A-4

```
rat    GTGAATTTCA CTCTGGGAGA CGATGCAAGC CTGGCCCTCA CCAGCGCCCT GATCTCTATC CCTGGCAAAG ACCTA  1476
mouse  GTGAATTTCA CTCTGGGAGA TGATGCAAGC CTGGCCCTCA CCAGCACCCT GATCTCTATC CCTGGCAAAG ACCCA  1482
human  GTGAACCTCA CCCTGGGGGA TGACACAAGC CTGGCTCTCA CGAGCACCCT GATTTCTGTT CCTGACAGAG ACCCA  1434 rat    GGCTCCCCTC TGAGAACAGT GAATGGTGTC CTGATCTCCA TTGGCTGCCT GGCCATGTTT GTCACCATGG TTACC  1551
mouse  GACTCCCCTC TGAGAGCAGT GAATGGTGTC CTGATCTCCA TCGGCTGCCT GGCTGTGCTT GTCACCATGG TTACC  1557
human  GCCTCGCCTT TAAGGATGGC AAACAGTGCC CTGATCTCCG TTGGCTGCTT GGCCATATTT GTCACTGTGA TCTCC  1509 rat    ATCTTGCTGT ACAAAAAACA CAAGACGTAC AAGCCAATAG GAAACTGCAC CAGGAACGTG GTCAAGGGCA AAGGC  1626
mouse  ATCTTGCTGT ACAAAAAACA CAAGGCGTAC AAGCCAATAG GAAACTGCCC CAGGAACACG GTCAAGGGCA AGGGC  1632
human  CTCTTGGTGT ACAAAAAACA CAAGGAATAC AACCCAATAG AAAATAGTCC TGGGAATGTG GTCAGAAGCA AAGGC  1584 rat    CTGAGTGTTT TTCTCAGCCA TGCAAAAGCC CCGTTCTCCC GAGGAGACCG GGAGAAGGAT CCACTGCTCC AGGAC  1701
mouse  CTGAGTGTTC TCCTCAGTCA CGCGAAAGCC CCGTTCTTCC GAGGAGACCA GGAGAAGGAT CCATTGCTCC AGGAC  1707
human  CTGAGTGTCT TTCTCAACCG TGCAAAAGCC CGGGAAAACCA GGAAAAGGAT CCGCTACTC- ---AA       1655 rat    AAGCCATGGA TGCTCTAA--  ----------                              1719
mouse  AAGCCAAGGA CACTCTAA--  ----------                              1725
human  AAACCAAGAA ---TTTAAAG  GAGTTTCTTA A                            1683
```

| | | | | | | |
|---|---|---|---|---|---|---|
| rat   | MESLCGVLVF | LLLAAGLPLQ | AAKRFRDVLG | HEQYPDHMRE | NNQLRGWSSD | 50 |
| mouse | MESLCGVLGF | LLLAAGLPLQ | AAKRFRDVLG | HEQYPDHMRE | HNQLRGWSSD | 50 |
| human | MECLYYFLGF | LLLAARLPLD | AAKRFHDVLG | NERPSAYMRE | HNQLNGWSSD | 50 |
| rat   | ENEWDEQLYP | VWRRGEGRWK | DSWEGGRVQA | ALTSDSPALV | GSNITFVVNL | 100 |
| mouse | ENEWDEHLYP | VWRRGDGRWK | DSWEGGRVQA | VLTSDSPALV | GSNITFVVNL | 100 |
| human | ENDWNEKLYP | VWKRGDMRWK | NSWKGGRVQA | VLTSDSPALV | GSNITFAVNL | 100 |
| rat   | VFPRCQKEDA | NGNIVYERNC | RSDLELASDP | YVYNWTTGAD | DEDWEDNTSQ | 150 |
| mouse | VFPRCQKEDA | NGNIVYEKNC | RNDLGLTSDL | HVYNWTAGAD | DGDWEDGTSR | 150 |
| human | IFPRCQKEDA | NGNIVYEKNC | RNEAGLSADP | YVYNWTAWSE | DSDGENGTGQ | 150 |
| rat   | GQHLRFPDGK | PFPRPHGRKK | WNFVYVFHTL | GQYFQKLGQC | SARVSINTVN | 200 |
| mouse | SQHLRFPDRR | PFPRPHGWKK | WSFVYVFHTL | GQYFQKLGRC | SARVSINTVN | 200 |
| human | SHHNVFPDGK | PFPHHPGWRR | WNFIYVFHTL | GQYFQKLGRC | SVRVSVNTAN | 200 |
| rat   | LTVGPQVMEV | IVFRRHGRAY | IPISKVKDVY | VITDQIPIFV | TMYQKNDRNS | 250 |
| mouse | LTAGPQVMEV | TVFRRYGRAY | IPISKVKDVY | VITDQIPVFV | TMSQKNDRNL | 250 |
| human | VTLGPQLMEV | TVYRRHGRAY | VPIAQVKDVY | VVTDQIPVFV | TMFQKNDRNS | 250 |
| rat   | SDETFLRDLP | IFFDVLIHDP | SHFLNYSAIS | YKWNFGDNTG | LFVSNNHTLN | 300 |
| mouse | SDEIFLRDLP | IVFDVLIHDP | SHFLNDSAIS | YKWNFGDNTG | LFVSNNHTLN | 300 |
| human | SDETFLKDLP | IMFDVLIHDP | SHFLNYSTIN | YKWSFGDNTG | LFVSTNHTVN | 300 |

FIG. 2B-1

```
rat    HTYVLNGTFN ENLTVQTAVP GPCPSPTPS- -PSSSTSPSP ASSPSPTLST   348
mouse  HTYVLNGTFN LNLTVQTAVP GPCPPPSPST PPSPSTPPLP SPSPLPTLST   350
human  HTYVLNGTFS LNLTVKAAAP GPCPPPPP-- -----PPRP- ------SK    334 rat    PSPSLMPTGY KSMELSDISN ENCRINRYGY FRATITIVDG ILEVNIIQVA   398
mouse  PSPSLMPTGY KSMELSDISN ENCRINRYGY FRATITIVEG ILEVSIMQIA   400
human  PTPSLGPAGD NPLELSRIPD ENCQINRYGH FQATITIVEG ILEVNIIQMT   384 rat    DVPIPTLQPD NSLMDFIVTC KGATPTEACT IISDPTCQIA QNRVCSPVAV   448
mouse  DVPMPTPQPA NSLMDFTVTC KGATPMEACT IISDPTCQIA QNRVCSPVAV   450
human  DVLMPVPWPE SSLIDFVVTC QGSIPTEVCT IISDPTCEIT QNTVCSPVDV   434 rat    DELCLLSVRR AFNGSGTYCV NFTLGDDASL ALTSALISIP GKDLGSPLRT   498
mouse  DGLCLLSVRR AFNGSGTYCV NFTLGDDASL ALTSTLISIP GKDPDSPLRA   500
human  DEMCLLTVRR TFNGSGTYCV NLTLGDDTSL ALTSTLISVP DRDPASPLRM   484 rat    VNGVLISIGC LAMFVTMVTI LLYKKHKTYK PIGNCTRNVV KGKGLSVFLS   548
mouse  VNGVLISIGC LAVLVTMVTI LLYKKHKAYK PIGNCPRNTV KGKGLSVLLS   550
human  ANSALISVGC LAIFVTVISL LVYKKHKEYN PIENSPGNVV RSKGLSVFLN   534 rat    HAKAPFSRGD REKDPLLQDK PW--ML   572
mouse  HAKAPFFRGD QEKDPLLQDK PR--TL   574
human  RAKAVFFPGN QEKDPLLKNQ EFKGVS   560
```

FIG. 2B-2

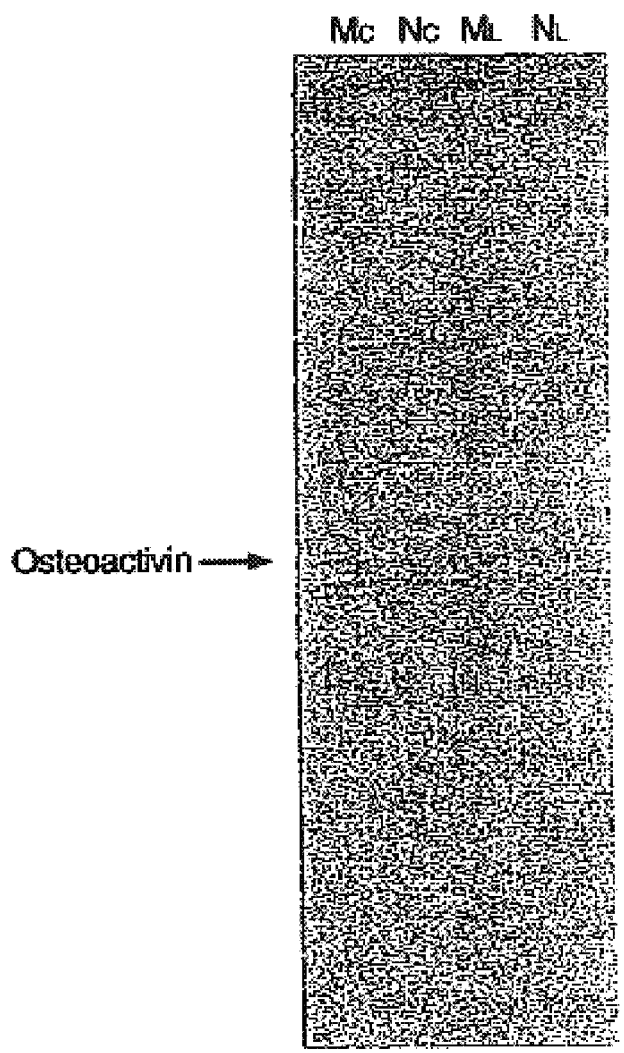
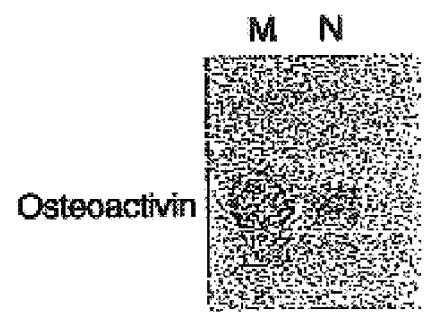
FIG. 4A
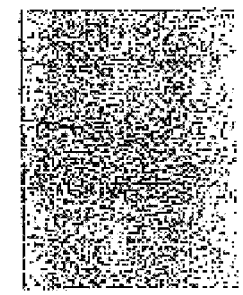
FIG. 4B
FIG. 3

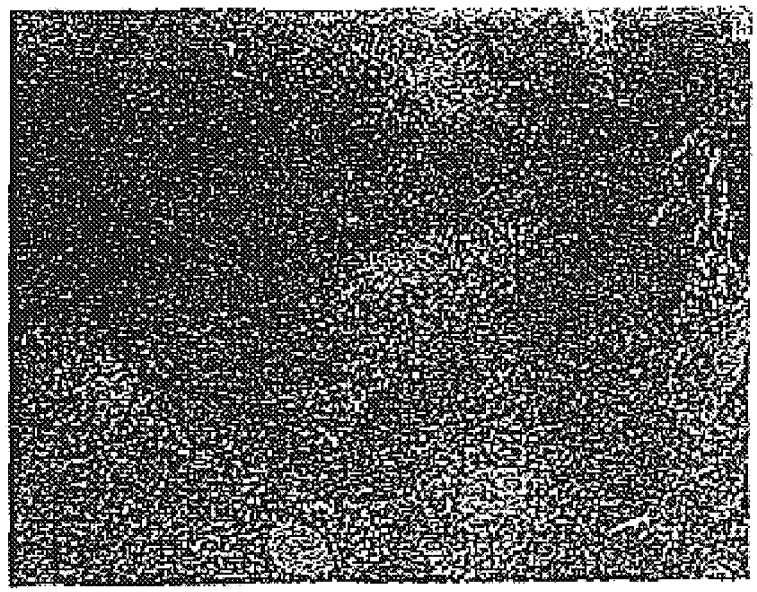
FIG. 5
 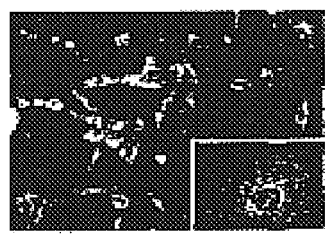 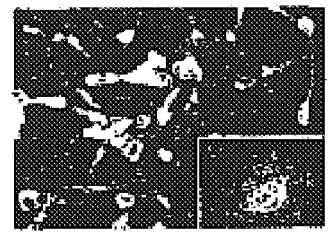
FIG. 5A    FIG. 5B    FIG. 5C

SEQUENCE LISTING

<160> NUMBER OF SEQ ID NOS: 8

<210> SEQ ID NO 1
<211> LENGTH: 2320
<212> TYPE: DNA
<213> ORGANISM: Rat osteoactivin
<220> FEATURE:
<221> NAME/KEY: CDS
<222> LOCATION: (115)...(1833)

<400> SEQUENCE: 1

```
gtatttcata aaacagagag gatcgcagga ggccggcact ctgactcctg gtggatggga      60
ctagggagtc agagtcaagc cctgactggc tgagggcggg cgctccgagt cagc atg     117
                                                              Met
                                                                1 gaa agt ctc tgc ggg gtc ctg gta ttt ctg ctg ctg gct gca gga ctg     165
Glu Ser Leu Cys Gly Val Leu Val Phe Leu Leu Leu Ala Ala Gly Leu
        5                   10                  15
```

-continued

| | | |
|---|---|---|
| ccg ctc cag gcg gcc aag cgg ttc cgt gat gtg ctg ggc cat gag cag<br>Pro Leu Gln Ala Ala Lys Arg Phe Arg Asp Val Leu Gly His Glu Gln<br>20　　　　　　25　　　　　　　30 | 213 | |
| tat ccg gat cac atg agg gag aac aac caa tta cgt ggc tgg tct tca<br>Tyr Pro Asp His Met Arg Glu Asn Asn Gln Leu Arg Gly Trp Ser Ser<br>35　　　　　　　40　　　　　　　45 | 261 | |
| gat gaa aat gaa tgg gat gaa cag ctg tat cca gtg tgg agg agg gga<br>Asp Glu Asn Glu Trp Asp Glu Gln Leu Tyr Pro Val Trp Arg Arg Gly<br>50　　　　　　　55　　　　　　　60　　　　　　　65 | 309 | |
| gag ggc aga tgg aag gac tcc tgg gaa gga ggc cgt gtg cag gca gcc<br>Glu Gly Arg Trp Lys Asp Ser Trp Glu Gly Gly Arg Val Gln Ala Ala<br>70　　　　　　　75　　　　　　　80 | 357 | |
| cta acc agt gat tca ccg gcc ttg gtg ggt tcc aat atc acc ttc gta<br>Leu Thr Ser Asp Ser Pro Ala Leu Val Gly Ser Asn Ile Thr Phe Val<br>85　　　　　　　90　　　　　　　95 | 405 | |
| gtg aac ctg gtg ttc ccc aga tgc cag aag gaa gat gcc aac ggc aat<br>Val Asn Leu Val Phe Pro Arg Cys Gln Lys Glu Asp Ala Asn Gly Asn<br>100　　　　　　105　　　　　　　110 | 453 | |
| atc gtc tat gag agg aac tgc aga agt gat ttg gag ctg gct tct gac<br>Ile Val Tyr Glu Arg Asn Cys Arg Ser Asp Leu Glu Leu Ala Ser Asp<br>115　　　　　　120　　　　　　　125 | 501 | |
| ccg tat gtc tac aac tgg acc aca ggg gca gac gat gag gac tgg gaa<br>Pro Tyr Val Tyr Asn Trp Thr Thr Gly Ala Asp Asp Glu Asp Trp Glu<br>130　　　　　　135　　　　　　　140　　　　　　145 | 549 | |
| gac aac acc agc caa ggc cag cac ctc agg ttc ccc gac ggg aag ccc<br>Asp Asn Thr Ser Gln Gly Gln His Leu Arg Phe Pro Asp Gly Lys Pro<br>150　　　　　　155　　　　　　　160 | 597 | |
| ttc cct cgc ccc cac gga cgg aag aaa tgg aac ttc gtc tac gtc ttc<br>Phe Pro Arg Pro His Gly Arg Lys Lys Trp Asn Phe Val Tyr Val Phe<br>165　　　　　　170　　　　　　　175 | 645 | |
| cac aca ctt ggt cag tat ttt caa aag ctg ggt cag tgt tca gca cga<br>His Thr Leu Gly Gln Tyr Phe Gln Lys Leu Gly Gln Cys Ser Ala Arg<br>180　　　　　　185　　　　　　　190 | 693 | |
| gtt tct ata aac aca gtc aac ttg aca gtt ggc cct cag gtc atg gaa<br>Val Ser Ile Asn Thr Val Asn Leu Thr Val Gly Pro Gln Val Met Glu<br>195　　　　　　200　　　　　　　205 | 741 | |
| gtg att gtc ttt cga aga cac ggc cgg gca tac att ccc atc tcc aaa<br>Val Ile Val Phe Arg Arg His Gly Arg Ala Tyr Ile Pro Ile Ser Lys<br>210　　　　　　215　　　　　　　220　　　　　　225 | 789 | |
| gtg aaa gac gtg tat gtg ata aca gat cag atc cct ata ttc gtg acc<br>Val Lys Asp Val Tyr Val Ile Thr Asp Gln Ile Pro Ile Phe Val Thr<br>230　　　　　　235　　　　　　　240 | 837 | |
| atg tac cag aag aat gac cgg aac tcg tct gat gaa acc ttc ctc aga<br>Met Tyr Gln Lys Asn Asp Arg Asn Ser Ser Asp Glu Thr Phe Leu Arg<br>245　　　　　　250　　　　　　　255 | 885 | |
| gac ctc ccc att ttc ttc gat gtc ctc att cac gat ccc agt cat ttc<br>Asp Leu Pro Ile Phe Phe Asp Val Leu Ile His Asp Pro Ser His Phe<br>260　　　　　　265　　　　　　　270 | 933 | |
| ctc aac tac tct gcc att tcc tac aag tgg aac ttt ggg gac aac act<br>Leu Asn Tyr Ser Ala Ile Ser Tyr Lys Trp Asn Phe Gly Asp Asn Thr<br>275　　　　　　280　　　　　　　285 | 981 | |
| ggc ctg ttt gtc tcc aac aat cac act ttg aat cac acg tat gtg ctc<br>Gly Leu Phe Val Ser Asn Asn His Thr Leu Asn His Thr Tyr Val Leu<br>290　　　　　　295　　　　　　　300　　　　　　305 | 1029 | |
| aat gga acc ttc aac ttt aac ctc acc gtg caa act gca gtg ccg gga<br>Asn Gly Thr Phe Asn Phe Asn Leu Thr Val Gln Thr Ala Val Pro Gly<br>310　　　　　　315　　　　　　　320 | 1077 | |
| cca tgc ccc tca ccc aca cct tcg cct tct tct tcg act tct cct tcg<br>Pro Cys Pro Ser Pro Thr Pro Ser Pro Ser Ser Ser Thr Ser Pro Ser<br>325　　　　　　330　　　　　　　335 | 1125 | |

```
cct gca tct tcg cct tca ccc aca tta tca aca cct agt ccc tct tta     1173
Pro Ala Ser Ser Pro Ser Pro Thr Leu Ser Thr Pro Ser Pro Ser Leu
            340                 345                 350 atg cct act ggc tac aaa tcc atg gag ctg agt gac att tcc aat gaa     1221
Met Pro Thr Gly Tyr Lys Ser Met Glu Leu Ser Asp Ile Ser Asn Glu
    355                 360                 365 aac tgc cga ata aac aga tat ggt tac ttc aga gcc acc atc aca att     1269
Asn Cys Arg Ile Asn Arg Tyr Gly Tyr Phe Arg Ala Thr Ile Thr Ile
370                 375                 380                 385 gta gat gga atc cta gaa gtc aac atc atc cag gta gca gat gtc cca     1317
Val Asp Gly Ile Leu Glu Val Asn Ile Ile Gln Val Ala Asp Val Pro
                390                 395                 400 atc ccc aca ctg cag cct gac aac tca ctg atg gac ttc att gtg acc     1365
Ile Pro Thr Leu Gln Pro Asp Asn Ser Leu Met Asp Phe Ile Val Thr
            405                 410                 415 tgc aaa ggg gcc act ccc acg gaa gcc tgt acg atc atc tct gac ccc     1413
Cys Lys Gly Ala Thr Pro Thr Glu Ala Cys Thr Ile Ile Ser Asp Pro
        420                 425                 430 acc tgc cag atc gcc cag aac agg gtg tgc agc ccg gtg gct gtg gat     1461
Thr Cys Gln Ile Ala Gln Asn Arg Val Cys Ser Pro Val Ala Val Asp
    435                 440                 445 gag ctg tgc ctc ctg tcc gtg agg aga gcc ttc aat ggg tcc ggc acg     1509
Glu Leu Cys Leu Leu Ser Val Arg Arg Ala Phe Asn Gly Ser Gly Thr
450                 455                 460                 465 tac tgt gtg aat ttc act ctg gga gac gat gca agc ctg gcc ctc acc     1557
Tyr Cys Val Asn Phe Thr Leu Gly Asp Asp Ala Ser Leu Ala Leu Thr
                470                 475                 480 agc gcc ctg atc tct atc cct ggc aaa gac cta ggc tcc cct ctg aga     1605
Ser Ala Leu Ile Ser Ile Pro Gly Lys Asp Leu Gly Ser Pro Leu Arg
            485                 490                 495 aca gtg aat ggt gtc ctg atc tcc att ggc tgc ctg gcc atg ttt gtc     1653
Thr Val Asn Gly Val Leu Ile Ser Ile Gly Cys Leu Ala Met Phe Val
        500                 505                 510 acc atg gtt acc atc ttg ctg tac aaa aaa cac aag acg tac aag cca     1701
Thr Met Val Thr Ile Leu Leu Tyr Lys Lys His Lys Thr Tyr Lys Pro
    515                 520                 525 ata gga aac tgc acc agg aac gtg gtc aag ggc aaa ggc ctg agt gtt     1749
Ile Gly Asn Cys Thr Arg Asn Val Val Lys Gly Lys Gly Leu Ser Val
530                 535                 540                 545 ttt ctc agc cat gca aaa gcc ccg ttc tcc cga gga gac cgg gag aag     1797
Phe Leu Ser His Ala Lys Ala Pro Phe Ser Arg Gly Asp Arg Glu Lys
                550                 555                 560 gat cca ctg ctc cag gac aag cca tgg atg ctc taa gtcttcactc          1843
Asp Pro Leu Leu Gln Asp Lys Pro Trp Met Leu  *
            565                 570 tcacttctga ctgggaaccc actcttctgt gcatgtatgt gagctgtgca gaagtacatg   1903
actggtagct gttgttttct acggattatt gtaaaatgta tatcatggtt tagggagtgt   1963
agttaattgg cattttagtg aagggatggg aagacagtat ttcttcgcat ctgtattgtg   2023 gttttttatac tgttaatagg gtgggcacat tgtgtctgaa gggggagggg gaggtcactg  2083
ctacttaagg tcctaggtta actgggagag gatgccccag gctccttaga tttctacaca  2143
agatgtgcct gaaccagct agtcctgacc taaaggccat gcttcatcaa ctctatctca   2203
gctcattgaa cataccctgag cgcctgatgg aattataatg gaaccaagct tgttgtatgg  2263
tgtgtgtgtg tacataagat actcattaaa aagacagtct attaaaaaaa aaaaaaa     2320
```

```
<210> SEQ ID NO 2
<211> LENGTH: 572
<212> TYPE: PRT
<213> ORGANISM: Rat osteoactivin

<400> SEQUENCE: 2

Met Glu Ser Leu Cys Gly Val Leu Val Phe Leu Leu Leu Ala Ala Gly
 1               5                  10                  15

Leu Pro Leu Gln Ala Ala Lys Arg Phe Arg Asp Val Leu Gly His Glu
             20                  25                  30

Gln Tyr Pro Asp His Met Arg Glu Asn Asn Gln Leu Arg Gly Trp Ser
         35                  40                  45

Ser Asp Glu Asn Glu Trp Asp Glu Gln Leu Tyr Pro Val Trp Arg Arg
 50                  55                  60

Gly Glu Gly Arg Trp Lys Asp Ser Trp Glu Gly Arg Val Gln Ala
 65                  70                  75                  80

Ala Leu Thr Ser Asp Ser Pro Ala Leu Val Gly Ser Asn Ile Thr Phe
             85                  90                  95

Val Val Asn Leu Val Phe Pro Arg Cys Gln Lys Glu Asp Ala Asn Gly
            100                 105                 110

Asn Ile Val Tyr Glu Arg Asn Cys Arg Ser Asp Leu Glu Leu Ala Ser
            115                 120                 125

Asp Pro Tyr Val Tyr Asn Trp Thr Thr Gly Ala Asp Asp Glu Asp Trp
        130                 135                 140

Glu Asp Asn Thr Ser Gln Gly Gln His Leu Arg Phe Pro Asp Gly Lys
145                 150                 155                 160

Pro Phe Pro Arg Pro His Gly Arg Lys Lys Trp Asn Phe Val Tyr Val
                165                 170                 175

Phe His Thr Leu Gly Gln Tyr Phe Gln Lys Leu Gly Gln Cys Ser Ala
            180                 185                 190

Arg Val Ser Ile Asn Thr Val Asn Leu Thr Val Gly Pro Gln Val Met
        195                 200                 205

Glu Val Ile Val Phe Arg Arg His Gly Arg Ala Tyr Ile Pro Ile Ser
    210                 215                 220

Lys Val Lys Asp Val Tyr Val Ile Thr Asp Gln Ile Pro Ile Phe Val
225                 230                 235                 240

Thr Met Tyr Gln Lys Asn Asp Arg Asn Ser Ser Asp Glu Thr Phe Leu
                245                 250                 255

Arg Asp Leu Pro Ile Phe Phe Asp Val Leu Ile His Asp Pro Ser His
            260                 265                 270

Phe Leu Asn Tyr Ser Ala Ile Ser Tyr Lys Trp Asn Phe Gly Asp Asn
        275                 280                 285

Thr Gly Leu Phe Val Ser Asn Asn His Thr Leu Asn His Thr Tyr Val
    290                 295                 300

Leu Asn Gly Thr Phe Asn Phe Asn Leu Thr Val Gln Thr Ala Val Pro
305                 310                 315                 320

Gly Pro Cys Pro Ser Pro Thr Pro Ser Pro Ser Ser Thr Ser Pro
                325                 330                 335

Ser Pro Ala Ser Ser Pro Ser Pro Thr Leu Ser Thr Pro Ser Pro Ser
            340                 345                 350

Leu Met Pro Thr Gly Tyr Lys Ser Met Glu Leu Ser Asp Ile Ser Asn
        355                 360                 365

Glu Asn Cys Arg Ile Asn Arg Tyr Gly Tyr Phe Arg Ala Thr Ile Thr
    370                 375                 380
```

```
Ile Val Asp Gly Ile Leu Glu Val Asn Ile Ile Gln Val Ala Asp Val
385                 390                 395                 400

Pro Ile Pro Thr Leu Gln Pro Asp Asn Ser Leu Met Asp Phe Ile Val
            405                 410                 415

Thr Cys Lys Gly Ala Thr Pro Thr Glu Ala Cys Thr Ile Ile Ser Asp
        420                 425                 430

Pro Thr Cys Gln Ile Ala Gln Asn Arg Val Cys Ser Pro Val Ala Val
        435                 440                 445

Asp Glu Leu Cys Leu Leu Ser Val Arg Arg Ala Phe Asn Gly Ser Gly
    450                 455                 460

Thr Tyr Cys Val Asn Phe Thr Leu Gly Asp Asp Ala Ser Leu Ala Leu
465                 470                 475                 480

Thr Ser Ala Leu Ile Ser Ile Pro Gly Lys Asp Leu Gly Ser Pro Leu
                485                 490                 495

Arg Thr Val Asn Gly Val Leu Ile Ser Ile Gly Cys Leu Ala Met Phe
            500                 505                 510

Val Thr Met Val Thr Ile Leu Leu Tyr Lys Lys His Lys Thr Tyr Lys
        515                 520                 525

Pro Ile Gly Asn Cys Thr Arg Asn Val Val Lys Gly Lys Gly Leu Ser
        530                 535                 540

Val Phe Leu Ser His Ala Lys Ala Pro Phe Ser Arg Gly Asp Arg Glu
545                 550                 555                 560

Lys Asp Pro Leu Leu Gln Asp Lys Pro Trp Met Leu
                565                 570

<210> SEQ ID NO 3
<211> LENGTH: 18
<212> TYPE: PRT
<213> ORGANISM: Rat osteoactivin

<400> SEQUENCE: 3

Cys Pro Asp His Met Arg Glu Asn Asn Gln Leu Arg Gly Trp Ser Ser
1               5                   10                  15

Asp Glu

<210> SEQ ID NO 4
<211> LENGTH: 19
<212> TYPE: PRT
<213> ORGANISM: Rat osteoactivin

<400> SEQUENCE: 4

Lys Ala Pro Phe Ser Arg Gly Asp Arg Glu Lys Asp Pro Leu Leu Gln
1               5                   10                  15

Asp Lys Cys

<210> SEQ ID NO 5
<211> LENGTH: 574
<212> TYPE: PRT
<213> ORGANISM: Mouse

<400> SEQUENCE: 5

Met Glu Ser Leu Cys Gly Val Leu Gly Phe Leu Leu Leu Ala Ala Gly
1               5                   10                  15

Leu Pro Leu Gln Ala Ala Lys Arg Phe Arg Asp Val Leu Gly His Glu
            20                  25                  30

Gln Tyr Pro Asp His Met Arg Glu His Asn Gln Leu Arg Gly Trp Ser
        35                  40                  45
```

-continued

```
Ser Asp Glu Asn Glu Trp Asp Glu His Leu Tyr Pro Val Trp Arg Arg
 50                  55                  60
Gly Asp Gly Arg Trp Lys Asp Ser Trp Glu Gly Arg Val Gln Ala
 65                  70                  75                  80
Val Leu Thr Ser Asp Ser Pro Ala Leu Val Gly Ser Asn Ile Thr Phe
                 85                  90                  95
Val Val Asn Leu Val Phe Pro Arg Cys Gln Lys Glu Asp Ala Asn Gly
            100                 105                 110
Asn Ile Val Tyr Glu Lys Asn Cys Arg Asn Asp Leu Gly Leu Thr Ser
            115                 120                 125
Asp Leu His Val Tyr Asn Trp Thr Ala Gly Ala Asp Asp Gly Asp Trp
    130                 135                 140
Glu Asp Gly Thr Ser Arg Ser Gln His Leu Arg Phe Pro Asp Arg Arg
145                 150                 155                 160
Pro Phe Pro Arg Pro His Gly Trp Lys Lys Trp Ser Phe Val Tyr Val
                165                 170                 175
Phe His Thr Leu Gly Gln Tyr Phe Gln Lys Leu Gly Arg Cys Ser Ala
            180                 185                 190
Arg Val Ser Ile Asn Thr Val Asn Leu Thr Ala Gly Pro Gln Val Met
            195                 200                 205
Glu Val Thr Val Phe Arg Arg Tyr Gly Arg Ala Tyr Ile Pro Ile Ser
    210                 215                 220
Lys Val Lys Asp Val Tyr Val Ile Thr Asp Gln Ile Pro Val Phe Val
225                 230                 235                 240
Thr Met Ser Gln Lys Asn Asp Arg Asn Leu Ser Asp Glu Ile Phe Leu
                245                 250                 255
Arg Asp Leu Pro Ile Val Phe Asp Val Leu Ile His Asp Pro Ser His
            260                 265                 270
Phe Leu Asn Asp Ser Ala Ile Ser Tyr Lys Trp Asn Phe Gly Asp Asn
    275                 280                 285
Thr Gly Leu Phe Val Ser Asn Asn His Thr Leu Asn His Thr Tyr Val
    290                 295                 300
Leu Asn Gly Thr Phe Asn Leu Asn Leu Thr Val Gln Thr Ala Val Pro
305                 310                 315                 320
Gly Pro Cys Pro Pro Ser Pro Ser Thr Pro Pro Ser Pro Ser Thr
                325                 330                 335
Pro Pro Leu Pro Ser Pro Ser Pro Leu Pro Thr Leu Ser Thr Pro Ser
            340                 345                 350
Pro Ser Leu Met Pro Thr Gly Tyr Lys Ser Met Glu Leu Ser Asp Ile
            355                 360                 365
Ser Asn Glu Asn Cys Arg Ile Asn Arg Tyr Gly Tyr Phe Arg Ala Thr
    370                 375                 380
Ile Thr Ile Val Glu Gly Ile Leu Glu Val Ser Ile Met Gln Ile Ala
385                 390                 395                 400
Asp Val Pro Met Pro Thr Pro Gln Pro Ala Asn Ser Leu Met Asp Phe
                405                 410                 415
Thr Val Thr Cys Lys Gly Ala Thr Pro Met Glu Ala Cys Thr Ile Ile
            420                 425                 430
Ser Asp Pro Thr Cys Gln Ile Ala Gln Asn Arg Val Cys Ser Pro Val
            435                 440                 445
Ala Val Asp Gly Leu Cys Leu Leu Ser Val Arg Arg Ala Phe Asn Gly
450                 455                 460
```

-continued

Ser Gly Thr Tyr Cys Val Asn Phe Thr Leu Gly Asp Asp Ala Ser Leu
465                 470                 475                 480

Ala Leu Thr Ser Thr Leu Ile Ser Ile Pro Gly Lys Asp Pro Asp Ser
            485                 490                 495

Pro Leu Arg Ala Val Asn Gly Val Leu Ile Ser Ile Gly Cys Leu Ala
        500                 505                 510

Val Leu Val Thr Met Val Thr Ile Leu Leu Tyr Lys Lys His Lys Ala
    515                 520                 525

Tyr Lys Pro Ile Gly Asn Cys Pro Arg Asn Thr Val Lys Gly Lys Gly
530                 535                 540

Leu Ser Val Leu Leu Ser His Ala Lys Ala Pro Phe Phe Arg Gly Asp
545                 550                 555                 560

Gln Glu Lys Asp Pro Leu Leu Gln Asp Lys Pro Arg Thr Leu
                565                 570

<210> SEQ ID NO 6
<211> LENGTH: 560
<212> TYPE: PRT
<213> ORGANISM: Human

<400> SEQUENCE: 6

Met Glu Cys Leu Tyr Tyr Phe Leu Gly Phe Leu Leu Leu Ala Ala Arg
1               5                   10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
50                  55                  60

Gly Asp Met Arg Trp Lys Asn Ser Trp Lys Gly Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
            260                 265                 270

```
Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
        290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Arg Pro Ser Lys Pro Thr
                325                 330                 335

Pro Ser Leu Gly Pro Ala Gly Asp Asn Pro Leu Glu Leu Ser Arg Ile
            340                 345                 350

Pro Asp Glu Asn Cys Gln Ile Asn Arg Tyr Gly His Phe Gln Ala Thr
        355                 360                 365

Ile Thr Ile Val Glu Gly Ile Leu Glu Val Asn Ile Ile Gln Met Thr
        370                 375                 380

Asp Val Leu Met Pro Val Pro Trp Pro Glu Ser Ser Leu Ile Asp Phe
385                 390                 395                 400

Val Val Thr Cys Gln Gly Ser Ile Pro Thr Glu Val Cys Thr Ile Ile
                405                 410                 415

Ser Asp Pro Thr Cys Glu Ile Thr Gln Asn Thr Val Cys Ser Pro Val
                420                 425                 430

Asp Val Asp Glu Met Cys Leu Leu Thr Val Arg Arg Thr Phe Asn Gly
            435                 440                 445

Ser Gly Thr Tyr Cys Val Asn Leu Thr Leu Gly Asp Asp Thr Ser Leu
        450                 455                 460

Ala Leu Thr Ser Thr Leu Ile Ser Val Pro Asp Arg Asp Pro Ala Ser
465                 470                 475                 480

Pro Leu Arg Met Ala Asn Ser Ala Leu Ile Ser Val Gly Cys Leu Ala
                485                 490                 495

Ile Phe Val Thr Val Ile Ser Leu Leu Val Tyr Lys Lys His Lys Glu
                500                 505                 510

Tyr Asn Pro Ile Glu Asn Ser Pro Gly Asn Val Val Arg Ser Lys Gly
            515                 520                 525

Leu Ser Val Phe Leu Asn Arg Ala Lys Ala Val Phe Phe Pro Gly Asn
        530                 535                 540

Gln Glu Lys Asp Pro Leu Leu Lys Asn Gln Glu Phe Lys Gly Val Ser
545                 550                 555                 560

<210> SEQ ID NO 7
<211> LENGTH: 1725
<212> TYPE: DNA
<213> ORGANISM: Mouse

<400> SEQUENCE: 7
atggaaagtc tctgcggggt cctgggattt ctgctgctgg ctgcaggact gcctctccag      60
gctgccaagc gatttcgtga tgtgctgggc catgaacagt atcccgatca catgagagag     120
cacaaccaat acgtggctg gtcttcggat gaaaatgaat gggatgaaca cctgtatcca      180
gtgtggagga ggggagacgg caggtggaag gactcctggg aaggaggccg tgtgcaggca     240 gtccctgacca gtgactcacc ggctctggtg ggttccaata tcacttttgt ggtgaacctg     300
gtgttcccca gatgccagaa ggaagatgct aatggcaata tcgtctatga aagaactgc     360 aggaatgatt tgggactgac atctgacctg catgtctaca actggactgc aggggcagat     420
gatggtgact gggaagatgg caccagccga agccagcatc tcaggttccc ggacaggagg     480
cccttccctc gccccatgg atggaagaaa tggagctttg tctacgtctt tcacacactt     540
```

| | | | |
|---|---|---|---|
| ggccagtatt | tccaaaaact | gggtcggtgt | tcagcacggg | tttctataaa cacagtcaac | 600 |
| ttgacagctg | gccctcaggt | catggaagtg | actgtctttc | gaagatacgg ccgggcatac | 660 |
| attcccatct | cgaaggtgaa | agatgtgtat | gtgataacag | atcagatccc tgtattcgtg | 720 |
| accatgtccc | agaagaatga | caggaacttg | tctgatgaga | tcttcctcag agacctcccc | 780 |
| atcgtcttcg | atgtcctcat | tcatgatccc | agccacttcc | tcaacgactc tgccatttcc | 840 |
| tacaagtgga | actttgggga | caacactggc | ctgtttgtct | ccaacaatca cactttgaat | 900 |
| cacacttatg | tgctcaatgg | aaccttcaac | cttaacctca | ccgtgcaaac tgcagtgccc | 960 |
| gggccatgcc | ctcccccttc | gccttcgact | ccgccttcac | cttcaactcc gcccttacct | 1020 |
| tcgccctcac | ctttgcccac | attatcaaca | cctagcccct | cttttaatgcc tactggttac | 1080 |
| aaatccatgg | agctgagtga | catttccaat | gaaaactgcc | gaataaacag ataaggctac | 1140 |
| ttcagagcca | ccatcacaat | tgtagagggg | atcctggaag | tcagcatcat gcagatagca | 1200 |
| gatgtcccca | tgcccacacc | gcagcctgcc | aactccctga | tggacttcac tgtgacctgc | 1260 |
| aaagggccca | cccccatgga | agcctgtacg | atcatctccg | accccacctg ccagatcgcc | 1320 |
| cagaaccggg | tctgcagccc | tgtggctgtg | atgggctgt | gcctgctgtc tgtgagaaga | 1380 |
| gccttcaatg | ggtctggcac | ctactgtgtg | aatttcactc | tgggagatga tgcaagcctg | 1440 |
| gccctcacca | gcaccctgat | ctctatccct | ggcaaagacc | cagactcccc tctgagagca | 1500 |
| gtgaatggtg | tcctgatctc | catcggctgc | ctggctgtgc | ttgtcaccat ggttaccatc | 1560 |
| ttgctgtaca | aaaaacacaa | ggcgtacaag | ccaataggaa | actgccccag gaacacggtc | 1620 |
| aagggcaagg | gcctgagtgt | tctcctcagt | cacgcgaaag | ccccgttctt ccgaggagac | 1680 |
| caggagaagg | atccattgct | ccaggacaag | ccaaggacac | tctaa | 1725 |

<210> SEQ ID NO 8
<211> LENGTH: 1683
<212> TYPE: DNA
<213> ORGANISM: Human

<400> SEQUENCE: 8

| | | | | |
|---|---|---|---|---|---|
| atggaaagtc | tctactattt | cctgggattt | ctgctcctgg | ctgcaagatt gccacttgat | 60 |
| gcccccaaac | gatttcatga | tgtgctgggc | aatgaaagac | cttctgctta catgagggag | 120 |
| cacaatcaat | taaatggctg | gtcttctgat | gaaaatgact | ggaatgaaaa actctaccca | 180 |
| gtgtggaagc | ggggagacat | gaggtggaaa | aactcctgga | agggaggccg tgtgcaggcg | 240 |
| gtcctgacca | gtgactcacc | agccctcgtg | ggctcaaata | taacatttgc ggtgaacctg | 300 |
| atattcccta | gatgccaaaa | ggaagatgcc | aatggcaaca | tagtctatga aagaactgc | 360 |
| agaaatgagg | ctggtttatc | tgctgatcca | tatgtttaca | ctggacagc atggtcagag | 420 |
| gacagtgacg | gggaaaatgg | caccggccaa | agccatcata | cgtcttccc tgatgggaaa | 480 |
| ccttttcctc | accaccccgg | atggagaaga | tggaatttca | tctacgtctt ccacacactt | 540 |
| ggtcagtatt | tccagaaatt | gggacgatgt | tcagtgagag | tttctgtgaa cacagccaat | 600 |
| gtgacacttg | gcctcaact | catggaagtg | actgtctaca | gaagacatgg acgggcatat | 660 |
| gttcccatcg | cacaagtgaa | agatgtgtac | gtggtaacag | atcagattcc tgtgtttgtg | 720 |
| actatgttcc | agaagaacga | tcgaaattca | tccgacgaaa | ccttcctcaa agatctcccc | 780 |
| attatgtttg | atgtcctgat | tcatgatcct | agccacttcc | tcaattattc taccattaac | 840 |
| tacaagtgga | gcttcgggga | taatactggc | ctgtttgttt | ccaccaatca tactgtgaat | 900 |
| cacacgtatg | tgctcaatgg | aaccttcagc | cttaacctca | ctgtgaaagc tgcagcacca | 960 |

-continued

| | |
|---|---|
| ggaccttgtc cgccaccgcc accaccaccc agaccttcaa aacccacccc ttctttagga | 1020 |
| cctgctggtg acaacccccct ggagctgagt aggattcctg atgaaaactg ccagattaac | 1080 |
| agataaggct actttcaagc caccatcaca attgtagagg gaatcttaga ggttaacatc | 1140 |
| atccagatga cagacgtcct gatgccggtg ccatggcctg aaagctccct aatagacttt | 1200 |
| gtcgtgacct gccaagggag cattcccacg gaggtctgta ccatcatttc tgaccccacc | 1260 |
| tgcgagatca cccagaacac agtctgcagc cctgtggatg tggatgagat gtgtctgctg | 1320 |
| actgtgagac gaaccttcaa tgggtctggg acgtactgtg tgaacctcac cctgggggat | 1380 |
| gacacaagcc tggctctcac gagcaccctg atttctgttc ctgacagaga cccagcctcg | 1440 |
| cctttaagga tggcaaacag tgccctgatc tccgttggct gcttggccat atttgtcact | 1500 |
| gtgatctccc tcttggtgta caaaaaacac aaggaataca acccaataga aaatagtcct | 1560 |
| gggaatgtgg tcagaagcaa aggcctgagt gtctttctca accgtgcaaa agccgtgttc | 1620 |
| ttcccgggaa accaggaaaa ggatccgcta ctcaaaaacc aagaatttaa aggagtttct | 1680 |
| taa | 1683 |

OSTEOACTIVIN PROTEIN AND NUCLEIC ACIDS ENCODING THE SAME, COMPOSITIONS AND METHODS OF STIMULATING BONE DIFFERENTIATION

CROSS REFERENCE TO RELATED APPLICATIONS

This application claims the benefit of U.S. Provisional Application No. 60/229,006, filed Aug. 30, 2000, now abandoned.

FIELD OF THE INVENTION

The present invention relates to the identification of an isolated, full-length rat nucleic acid molecule encoding an osteoactivin protein, therapeutic compositions comprising an osteoactivin protein, and methods for using the nucleic acid molecules and proteins for stimulating bone differentiation. The invention also relates to methods for treating bone disorders, including osteopetrosis and osteoporosis.

BACKGROUND OF THE INVENTION

The formation and maintenance of the vertebrate skeleton requires the interactions of many cell types and growth factors and other molecules. The past decade has witnessed an explosive growth in the general understanding of growth factors and other proteins that mediate the complex coordination of bone formation and bone resorption by these different cell types in skeletal modeling and remodeling (Popoff and Marks, *Oral and Maxillofacial Clinics of North America* 9:563–579 (1997)).

In general, the bone remodeling cycle involves a complex series of sequential steps that are highly regulated. The initial "activation" phase of bone remodeling begins early in fetal life and is dependent on the effects of local and systemic growth factors on mesenchymal cells of the osteoblast lineage (Eriksen, *Endocrinol. Rev.* 7:379–408 (1986)). These cells interact with hematopoietic precursors to form osteoclasts in the "resorption" phase. This leads to the differentiation, migration and fusion of the large multinucleated osteoclasts. These cells attach to the mineralized bone surface and initiate resorption by the secretion of hydrogen ions and lysosomal enzymes. Osteoclastic resorption produces irregular scalloped cavities on bone surface. Once the osteoclasts have completed their work of bone removal, there is a "reversal" phase during which mononuclear cells, which may be of the macrophage lineage, are present on the bone surface. These cells further degrade collagen, deposit proteoglycans, and release growth factors that signal the initiation of the "formation" phase. During the final formation phase of the remodeling cycle, the cavity created by resorption can be completely filled in with successive layers of osteoblasts, which differentiate from their mesenchymal precursors and lay down a mineralizable matrix. (Raisz, *Clin. Chem.* 45:1353–1358 (1999)).

With bone disorders associated with decreased bone mass, osteoclastic resorption outweighs osteoblastic bone formation, resulting in bone loss. While treatments that stimulate bone formation would be beneficial in treating or preventing bone loss, current therapies are suboptimal (Canalis, *J. Clin. Invest.* 106:177–179 (2000); Raisz, *J. Bone Min. Metab* 17:79–89 (1999)).

An animal model useful in bone studies is the osteopetrosis (op) mutation in the rat. Osteopetrosis describes a group of congenital bone disorders that are characterized by a generalized increase in skeletal mass resulting from a primary defect in osteoclast-mediated bone resorption (Popoff and Schneider, *Molec. Med. Today* 2:349–358 (1996)). Numerous osteopetrotic mutations have been described in other species, including human and mouse. The bone that is formed as the skeleton develops and grows in animals with this mutation is not resorbed, resulting in the failure to develop bone marrow cavities. The osteopetrotic mutations are pathogenetically heterogeneous since the point at which osteoclast development or activation is intercepted differs for each mutation (Popoff and Marks, *Bone* 17:437–445 (1995)). Although osteoclast hypofunction is universal among the osteopetrotic mutations, genetic abnormalities involving osteoblast development/function (i.e., bone formation), mineral homeostasis and the immune and endocrine systems have also been reported within this disorder (Seifert et al., *Clin. Orthop.* 294:23–33 (1993)).

To date, pharmaceutical approaches to managing osteoporosis or osteopetrosis are of limited effectiveness. Therefore, alternative therapies are needed to modulate bone cell differentiation and bone formation, and to treat bone disorders such as osteoporosis and osteopetrosis.

SUMMARY OF THE INVENTION

The present invention is based, in part, on the discovery of a novel rat gene encoding an osteoactivin protein. The nucleotide sequence of full-length cDNA of the gene is shown in SEQ ID NO:1. The nucleotide sequence of the cDNA encoding the osteoactivin protein is shown in nucleotides 115 to 1,830 of SEQ ID NO:1 and the corresponding amino acid sequence of the osteoactivin protein is shown in SEQ ID NO:2. The polynucleotide sequence of the cDNA encoding the osteoactivin protein lacking the signal sequence is shown in nucleotides 181–1830 of SEQ ID NO:1 and the corresponding osteoactivin polypeptide lacking the signal sequence is from amino acid residues 23–572 of SEQ ID NO:2. The claimed invention also relates to antibodies which recognize one or more epitopes of the osteoactivin protein. The claimed invention provides therapeutic compositions comprising (i) a nucleic acid molecule encoding an osteoactivin protein, (ii) an osteoactivin protein, or (iii) an antibody to an osteoactivin protein. These therapeutic compositions are useful to treat bone disorders and to stimulate bone formation and bone cell differentiation.

Accordingly, in one aspect, the invention is directed to molecules encoding an osteoactivin protein. One embodiment of this aspect is a nucleic acid molecule encoding a rat osteoactivin protein having a molecular weight of 63.8 kilodaltons (kD), wherein said osteoactivin protein stimulates bone cell differentiation. In a related embodiment of this aspect, the invention encompasses a full-length nucleic acid molecule which encodes an osteoactivin protein, wherein said nucleic acid comprises the nucleic acid sequence of SEQ ID NO:1. In another embodiment, the invention provides a nucleic acid molecule encoding an osteoactivin protein, wherein said nucleic acid hybridizes to the complement of SEQ ID NO:1 under moderately stringent conditions. In a preferred embodiment, the nucleic acid molecule encoding an osteoactivin protein having at least 92% sequence identity with the nucleic acid sequence of SEQ ID NO:1 is described. In some embodiments, the nucleic acid molecule encodes a polypeptide comprising SEQ ID NO:2. The invention also embodies the nucleic acid molecule encoding an osteoactivin polypeptide comprising amino acid residues 23–572 of SEQ ID NO:2. In other embodiments, the invention provides a nucleic acid encoding an osteoactivin protein, wherein said nucleic acid comprises from nucleotide 115 to nucleotide 1,830 of SEQ ID NO:1. Other embodiments of the invention provide a polynucleotide encoding an osteoactivin protein lacking the leader sequence, wherein said polynucleotide comprises from nucleic acid residues from 181 to1830 of SEQ ID NO:1. In still other embodiments, the invention provides a nucleic acid encoding an osteoactivin protein, wherein said nucleic acid molecule hybridizes to the complement of nucleotide 115 to nucleotide 1,830 of SEQ ID NO:1 under moderately stringent conditions. In yet another embodiment of this aspect, the invention further provides a nucleic acid molecule encoding an osteoactivin protein having at least 92% sequence identity with the nucleic acid sequence from nucleotide 115 to nucleotide 1,830 of SEQ ID NO:1.

As used herein, the term "nucleic acid molecule" includes DNA molecules (e.g., a cDNA or genomic DNA) and RNA molecules (e.g., an mRNA) and analogs of the DNA or RNA generated, e.g., by the use of nucleotide analogs. The nucleic acid molecule can be single-stranded or double-stranded, but preferably is double-stranded DNA. Nucleic acid molecules include naturally occurring nucleic acid molecules which are separated from other molecules which are present in the natural source of the nucleic acid. For example, a nucleic acid molecule includes genomic DNA which is separated from the chromosome with which the genomic DNA is naturally associated. Preferably, a naturally occurring nucleic acid molecule is free of sequences which naturally flank the nucleic acid (i.e., sequences located at the 5' and/or 3' ends of the nucleic acid) in the genomic DNA of the organism from which the nucleic acid is derived. For example, in various embodiments, the isolated nucleic acid molecule can contain less than 5 kilobases (kb), 4 kb, 3 kb, 2 kb, 1 kb, 0.5 kb or 0.1 kb of 5' and/or 3' nucleotide sequences which naturally flank the nucleic acid molecule in genomic DNA of the cell from which the nucleic acid is derived. Moreover, an isolated nucleic acid molecule, such as a cDNA molecule, is substantially free of other cellular material, or culture medium when produced by recombinant techniques, or substantially free of chemical precursors or other chemicals when chemically synthesized.

As used herein, the term "osteoactivin protein" refers to a protein including the amino acid sequence of SEQ ID NO:2, the murine osteoactivin protein homolog, nmb, of SEQ ID NO:5, the human osteoactivin protein homolog, nmb, of SEQ ID NO:6, and the amino acid sequence comprising amino acid residues 23–572 of SEQ ID NO:2. Further, an osteoactivin protein has at least 50% sequence identity, preferably 70% sequence identity, and more preferably 90% sequence identity to the amino acid sequence of SEQ ID NO:2, SEQ ID NO:5, or SEQ ID NO:6, and stimulates bone cell differentiation or bone formation. Preferably, the osteoactivin protein is naturally occurring in a mammalian species.

As used herein, "stimulates bone cell differentiation" means any increase in bone cell number or size, including without limitation, the increase in the rate of bone cell division or precursor bone cell recruitment from the stem cells or bone marrow cells, and an increase in bone cell size. Such bone cell differentiation can be measured by well known cell proliferation assays (e.g., $^3$H-thymidine incorporation) and bone differentiation assays (e.g., Owen, et al., *J. Cell Physiol.* 143:420–30 (1990)).

As used herein, by "stimulates bone formation" is meant the recruitment of osteoblasts or osteoblast precursors to a bone site, which results in differentiation of the cells into mature osteoblasts and their secretion of collagenous matrix which mineralizes into bone matter and increases bone mass at the site. This term also encompasses the increased production and secretion of collagenous matrix by mature osteoblasts.

As used herein, the term "hybridizes under moderately stringent conditions" describes conditions for hybridization and washing. Stringent conditions are known to those skilled in the art and can be found in *Current Protocols in Molecular Biology*, John Wiley & Sons, N.Y. (1989), 6.3.1–6.3.6. An example of moderately stringent hybridization conditions is hybridization in 50% formamide 6×SSC at 42° C., followed by one or more washes in 0.2×SSC, 0.1% sodium dodecyl sulfate (SDS) at 55° C. In some preferable embodiments, an isolated nucleic acid molecule of the invention that hybridizes under moderately stringent conditions to the sequence of SEQ ID NO:1 corresponds to a naturally-occurring nucleic acid molecule.

By two nucleic acid molecules being "complementary" to one another or hybridizing to a "complement" of another nucleic acid molecule is meant that the first nucleic acid molecule (e.g., an oligonucleotide) is able to form Watson-Crick base pair hydrogen bonds (i.e., hybridize) with the second nucleic acid molecule to form a duplex.

As used herein, a percent "sequence identity" refers to a calculation of "homology" or "identity" between two different nucleic acid or amino acid sequences (the terms are used interchangeably herein) when the sequences are aligned and compared. The percent sequence identity between the two sequences is a function of the number of identical positions shared by the sequences, taking into account the number of gaps, and the length of each gap, which need to be introduced for optimal alignment of the two sequences.

In another aspect of the invention, the invention features an isolated and substantially pure osteoactivin protein, or polypeptide fragment thereof. One preferred embodiment of this aspect of the invention is an isolated and substantially pure rat osteoactivin protein, or polypeptide fragment thereof, wherein said protein comprises the amino acid sequence of SEQ ID NO:2. In another embodiment, the invention provides an isolated and substantially pure, non-human, non-murine osteoactivin protein, or polypeptide fragment thereof, having at least 90% sequence identity with the amino acid sequence of SEQ ID NO:2, wherein said osteoactivin protein or polypeptide fragment thereof stimulates bone cell differentiation or bone formation.

An "isolated" or "purified" osteoactivin protein or polypeptide is substantially free of cellular material or other contaminating proteins from the cell or tissue source from which the protein is derived, or substantially free from chemical precursors or other chemicals when chemically synthesized. In one embodiment, the language "substantially free" means preparation of osteoactivin protein having less than 30%, 20%, 10% and more preferably less than 5% (by weight), of non-osteoactivin protein (also referred to herein as a "contaminating protein"), or of chemical precursors or non-osteoactivin compounds. When the osteoactivin protein, or biologically active portion thereof, is recombinantly produced, it is also preferably substantially free of culture medium, i.e., the culture medium represents less than 20%, more preferably less than 10%, and most preferably less than 5% of the volume of the protein preparation. The invention includes isolated or purified preparations of at least 0.01 milligrams, at least 0.1 milligrams, at least 1.0 milligrams, and at least 10 milligrams by weight.

Also included, in another aspect of the invention, are expression vectors containing nucleic acid molecules encoding an osteoactivin protein or polypeptide fragment therein. In one embodiment, the invention features a biologically functional expression vector comprising a nucleic acid sequence encoding an osteoactivin protein, or biologically active polypeptide fragment thereof, wherein said osteoactivin protein comprises the amino acid sequence of SEQ ID NO:2, or has at least 90% sequence identity to the amino acid sequence of SEQ ID NO:2, and which stimulates bone cell differentiation or bone formation.

In another embodiment of this aspect, the invention is directed to biologically functional expression vectors comprising a nucleic acid molecule encoding a rat osteoactivin protein having a molecular weight of 63.8 kD, wherein said osteoactivin protein stimulates bone cell differentiation. In another embodiment, a biologically functional expression vector is provided which comprises the nucleic acid sequence of SEQ ID NO:1. The invention also encompasses a biologically functional expression vector comprising said nucleic acid molecule encoding an osteoactivin protein, wherein the nucleic acid molecule hybridizes to the complement of SEQ ID NO:1 under moderately stringent conditions. The invention also provides a biologically functional expression vector comprising a nucleic acid molecule encoding an osteoactivin protein and having at least 92% sequence identity with the nucleic acid sequence of SEQ ID NO:1. In another embodiment, the invention provides a biologically functional expression vector comprising a nucleic acid molecule encoding an osteoactivin protein, wherein said nucleic acid molecule comprises from nucleotide 115 to nucleotide 1,830 of SEQ ID NO:1. Yet another embodiment of this aspect of the invention includes a biologically functional expression vector comprising a nucleic acid molecule encoding an osteoactivin protein, wherein said nucleic acid molecule hybridizes to the complement of nucleotide 115 to nucleotide 1,830 of SEQ ID NO:1 under moderately stringent conditions. Still yet another embodiment is directed to a biologically functional expression vector comprising said nucleic acid molecule encoding an osteoactivin protein having at least 92% sequence identity with the nucleic acid sequence from nucleotide 115 to nucleotide 1,830 of SEQ ID NO:1. In each of these embodiments, the vector may be a plasmid or a viral vector.

As used herein, the term "vector" refers to a composition capable of carrying a nucleic acid molecule to its target. Vectors include liposomes and nucleic acid molecules capable of transporting another nucleic acid to which it has been linked. Such nucleic acid vectors include plasmids, cosmids, or viral vectors. The nucleic acid vector can be capable of autonomous replication or it can integrate into a host DNA. Viral vectors include, e.g., replication defective retroviruses, adenoviruses and adeno-associated viruses. A "biologically functional expression vector" as used herein refers to a vector used to incorporate nucleic acid molecules of the invention, including an osteoactivin-encoding nucleic acid, in a form suitable for expression in a host cell.

In yet another aspect, the invention features immunoglobulins such as antibodies and antigen-binding fragments thereof, that recognize and bind one or more epitopes of the osteoactivin proteins or polypeptide fragments thereof. In one embodiment of this aspect, the invention provides a substantially pure antibody that specifically binds to one or more epitopes of an osteoactivin protein, or a polypeptide fragment thereof, wherein said osteoactivin protein stimulates bone cell differentiation. The invention further provides a substantially pure antibody that specifically binds to one or more epitopes of an osteoactivin protein, or a polypeptide fragment thereof, wherein said osteoactivin protein comprises the amino acid sequence of SEQ ID NO:6. In a related embodiment, a substantially pure antibody that specifically binds to one or more epitopes of an osteoactivin protein, or polypeptide fragment thereof, wherein said osteoactivin protein comprises the amino acid sequence of SEQ ID NO:2 is provided. In a preferred embodiment, the antibody is selected from the group consisting of an antibody which binds to one or more epitopes of an osteoactivin peptide 35 having SEQ ID NO:3 and an antibody which binds to one or more epitopes of an osteoactivin peptide 551 having SEQ ID NO:4. In a particularly preferred embodiment, the antibody binds to one or more epitopes of amino acids 538–553 of SEQ ID NO:6. Another preferred embodiment is an antibody which specifically binds to an osteoactivin protein, or polypeptide fragment thereof, having at least 90% sequence identity with the amino acid sequence of SEQ ID NO:2, wherein said osteoactivin protein or polypeptide fragment thereof stimulates bone cell differentiation or bone formation. In each of these embodiments, the antibody may be a polyclonal or a monoclonal antibody.

The term "antibody" as used herein refers to an immunoglobulin molecule or immunologically active portion thereof, i.e., an antigen-binding portion. Examples of immunologically active portions of immunoglobulin molecules include F(ab), Fv, and F(ab')$_2$ fragments which can be generated by cleaving the antibody with an enzyme such as pepsin.

The term "epitope" as used herein means that region of amino acid residues of an osteoactivin protein antigen that is specifically recognized by an anti-osteoactivin antibody.

By "specifically binds" means an antibody that physically interacts with its specific ligand (i.e., an osteoactivin protein or biologically active polypeptide fragment thereof) with greater affinity that it binds to other molecules.

The invention further provides methods for producing a substantially pure osteoactivin protein, or polypeptide fragment thereof, comprising: (a) culturing a cell stably transformed with a gene comprising a nucleic acid molecule encoding an osteoactivin protein, wherein said nucleic acid comprises the nucleic acid sequence from nucleotide 115 to nucleotide 1,830 of SEQ ID NO:1; and (b) isolating and purifying the osteoactivin protein from the culture medium. Another preferred embodiment includes a method for producing a substantially pure osteoactivin protein, or polypeptide fragment thereof, comprising: (a) culturing a cell stably transformed with a gene comprising said nucleic acid molecule encoding an osteoactivin protein having at least 92% sequence identity with the nucleic acid sequence from nucleotide 115 to nucleotide 1,830 of SEQ ID NO:1; and (b) isolating and purifying said osteoactivin protein from said culture medium. A method for producing a substantially pure osteoactivin protein, or polypeptide fragment thereof, comprising: (a) culturing a cell stably transfected with a vector comprising the nucleic acid molecule encoding an osteoactivin protein, wherein said nucleic acid comprises the nucleic acid sequence from nucleotide 115 to nucleotide 1,830 of SEQ ID NO:1; and (b) isolating and purifying said osteoactivin protein from said culture medium, is also provided. In a related embodiment, the invention provides a method for producing a substantially pure osteoactivin protein, or polypeptide fragment thereof, comprising: (a) culturing a cell stably transfected with a vector comprising said nucleic acid molecule encoding an osteoactivin protein having at least 92% sequence identity with the nucleic acid sequence from nucleotide 115 to nucleotide 1,830 of SEQ ID NO:1; and (b) isolating and purifying said osteoactivin protein from said culture medium.

As used herein, the terms osteoactivin "gene" and "recombinant gene" refer to nucleic acid molecules which include an open reading frame encoding an osteoactivin protein, such as a mammalian osteoactivin protein, and can further include non-coding regulatory sequences, and introns. These genes can be isolated from genomic DNA, cloned by recombinant means, or chemically synthesized.

As used herein, the terms "transformation" and "transfection" are intended to refer to a variety of art-recognized techniques for introducing foreign nucleic acid (e.g., DNA) into a prokaryotic or eukaryotic host cell, including, but not limited to, calcium phosphate or calcium chloride co-precipitation, DEAE-dextran-mediated transfection, lipofection, or electroporation, such that the DNA within the vector is expressed in the host cell.

The invention also provides for therapeutic compositions of the disclosed nucleic acid molecules and osteoactivin proteins and antibodies. Accordingly, in another aspect, the invention provides a therapeutic composition comprising a pharmaceutically acceptable carrier or delivery vehicle and a nucleic acid encoding an osteoactivin protein, or biologically active polypeptide fragment thereof, wherein said osteoactivin protein stimulates bone cell differentiation. In some embodiments, the therapeutic composition comprises a nucleic acid molecule encoding a human osteoactivin or encoding the amino acid sequence of SEQ ID NO:6. In still another embodiment, the invention encompasses a therapeutic composition comprising a nucleic acid molecule encoding an osteoactivin protein having at least 92% sequence identity with the nucleic acid sequence of SEQ ID NO:1, and a pharmaceutically acceptable delivery vehicle.

In certain embodiments of this aspect of the invention, the therapeutic composition further comprises a mediator such as a cytokine or a growth factor. Non-limiting examples of such mediators include interleukin-1, tumor necrosis factor, lymphotoxin, interleukin-6, prostaglandins of the E-series, leukotrienes, lipopolysaccharides, transforming growth factor-β, and colony-stimulating factors. In another related aspect, the invention provides a therapeutic composition comprising an agent that stimulates osteoactivin-mediated bone formation. The term "mediator" refers to a molecule that directly modulates, mediates, or changes the expression of an osteoactivin protein.

As used herein, a "therapeutic composition" refers to a composition comprising an active ingredient required to cause a desired effect when a therapeutically effective amount of the composition is administered to a mammal in need thereof.

Within the present invention, a "therapeutically effective amount" of a composition is that amount of each active component of the therapeutic composition that is sufficient to show a benefit (e.g., a reduction in a symptom associated with the disorder, disease, or condition being treated). When applied to an individual active ingredient, administered alone, the term refers to that ingredient alone. When applied to a combination, the term refers to combined amounts of the active ingredients that result in the benefit, whether administered in combination, serially, or simultaneously.

As used herein, the term "pharmaceutically acceptable delivery vehicle" refers to carriers that do not negatively affect the biological activity of the therapeutic molecule or compound to be placed therein. Preferably, the vehicle targets bone cells. The characteristics of the delivery vehicle will depend on the route of administration. Therapeutic compositions may contain, in addition to the active compound, diluents, fillers, salts, buffers, stabilizers, solubilizers, and other materials well known in the art.

Other therapeutic compositions within the scope of this invention cover compositions comprising vectors. Accordingly, in one embodiment, the invention features a therapeutic composition comprising a biologically functional expression vector comprising a nucleic acid sequence encoding an osteoactivin protein, wherein said osteoactivin protein stimulates bone cell differentiation or bone formation, and a pharmaceutically acceptable delivery vehicle. In another embodiment, the invention provides a therapeutic composition comprising a biologically functional expression vector comprising a nucleic acid molecule encoding an osteoactivin protein having at least 92% sequence identity with the nucleic acid sequence of SEQ ID NO:1, and a pharmaceutically acceptable delivery vehicle. In certain embodiments of this aspect of the invention, the therapeutic composition further comprises a mediator, such as interleukin-1, tumor necrosis factor, lymphotoxin, interleukin-6, prostaglandins of the E-series, leukotrienes, lipopolysaccharides, transforming growth factor-β, or colony-stimulating factors, or a nucleic acid molecule encoding any of these mediator polypeptides.

Still other embodiments within this aspect of the invention are directed to therapeutic compositions comprising an osteoactivin protein. Accordingly, the invention features a therapeutic composition comprising a pharmaceutically acceptable carrier or delivery vehicle and an osteoactivin protein, or biologically active polypeptide fragment thereof, wherein said osteoactivin protein stimulates bone cell differentiation or bone formation. In some embodiments, the osteoactivin protein in the therapeutic composition is human. In other embodiments, the osteoactivin protein comprises SEQ ID NO:6. In another embodiment of this aspect, the invention covers a therapeutic composition comprising an osteoactivin protein, or polypeptide fragment thereof, wherein said protein comprises the amino acid sequence of SEQ ID NO:2, and a pharmaceutically acceptable delivery vehicle. In yet a further embodiment, a therapeutic composition comprising a pharmaceutically acceptable delivery vehicle and a non-human, non-murine osteoactivin protein, or polypeptide fragment thereof, having at least 90% sequence identity with the amino acid sequence of SEQ ID NO:2, wherein said osteoactivin protein or polypeptide fragment thereof stimulates bone cell differentiation or bone formation. In certain embodiments of this aspect of the invention, the therapeutic composition may further comprises a mediator, including interleukin-1, tumor necrosis factor, lymphotoxin, interleukin-6, prostaglandins of the E-series, leukotrienes, lipopolysaccharides, transforming growth factor-β, and colony-stimulating factors. In another aspect, the invention provides a therapeutic composition comprising an agent that inhibits osteoactivin-mediated bone formation, and a pharmaceutically acceptable delivery vehicle.

As used herein, a "biologically active portion" of an osteoactivin protein includes a fragment of an osteoactivin protein which is capable of affecting bone differentiation or bone formation.

Additional therapeutic compositions of the invention relate to those comprising antibodies that react with, or specifically bind, osteoactivin proteins. In one embodiment of this aspect, the invention provides a therapeutic composition comprising a pharmaceutically acceptable delivery vehicle and an antibody that specifically binds to one or more epitopes of an osteoactivin protein, or polypeptide fragment thereof, wherein said osteoactivin protein stimulates bone differentiation or bone formation. In a related embodiment, the invention covers a therapeutic composition comprising a substantially pure antibody that specifically binds to one or more epitopes of an osteoactivin protein, or polypeptide fragment thereof, wherein said osteoactivin protein comprises the amino acid sequence of SEQ ID NO:2, and a pharmaceutically acceptable delivery vehicle. In a preferred embodiment, the antibody of a therapeutic composition is selected from the group consisting of an antibody which binds to one or more epitopes of an osteoactivin peptide 35 having SEQ ID NO:3, an antibody which binds to one or more epitopes of an osteoactivin peptide 551 having SEQ ID NO:4, and an antibody which binds to one or more epitopes of amino acids 538–553 of the human osteoactivin protein of SEQ ID NO:6, together with a pharmaceutically acceptable delivery vehicle. Another preferred antibody, according to this aspect of the invention, is one in which the antibody of the therapeutic composition specifically binds to a non-human, non-murine osteoactivin protein, or polypeptide fragment thereof, having at least 90% sequence identity with the amino acid sequence of SEQ ID NO:2, wherein said osteoactivin protein or polypeptide fragment thereof stimulates bone cell differentiation or bone formation, together with a pharmaceutically acceptable delivery vehicle. In certain embodiments, the antibody of the invention is a polyclonal or a monoclonal antibody.

In yet another aspect, the invention provides in vivo methods of stimulating bone formation in a mammal, comprising administering to said mammal a therapeutically effective amount of a nucleic acid molecule encoding an osteoactivin protein or peptide thereof, or an osteoactivin protein, or biologically active polypeptide fragment thereof, or an agent that enhances osteoactivin-mediated bone cell differentiation or bone formation. In other embodiments of this aspect, ex vivo methods for stimulating bone formation in a human are described, comprising the steps of: (a) extracting osteoblast cells from said human; (b) contacting said osteoblast cells with a therapeutically effective amount of a nucleic acid molecule encoding an osteoactivin protein, or an osteoactivin protein, or biologically active polypeptide fragment thereof; and (c) returning said cells to the bone of said human.

"Mammal" as used herein means any animal classified as a mammal including humans, cows, horses, dogs, mice, cats, goats, pigs, and sheep.

In another aspect, the invention features in vivo methods for inhibiting bone formation in a mammal, comprising administering to said mammal a therapeutically effective amount of any of the therapeutic compositions of the present invention comprising antibodies. In a related aspect, the invention also provides a method for inhibiting bone formation in a mammal, comprising administering to said mammal a therapeutically effective amount of an agent that inhibits osteoactivin-mediated bone formation.

In another aspect, the invention provides in vivo methods of inhibiting bone formation or bone cell differentiation in a mammal, comprising administering to said mammal a therapeutically effective amount of any of the therapeutic compositions of the invention comprising, in part, an antibody.

The invention provides, in yet another aspect, in vivo methods of treating bone disorders in a mammal, such as a human, comprising administering to said mammal a therapeutically effective amount of any of the therapeutic compositions of the invention, comprising an anti-osteoactivin antibody or an agent that inhibits osteoactivin-mediated bone differentiation. In a related embodiment, the invention provides ex vivo methods for treating bone disorders in a mammal, comprising the steps of: (a) extracting osteoblast cells from said mammal; (b) contacting said osteoblast cells with a therapeutically effective amount of an antibody specific for osteoactivin protein or an agent that inhibits osteoactivin-mediated bone cell differentiation or bone formation; and (c) returning said contacted cells to the bone of said mammal. In preferred embodiments, the bone disorder treated by the method is selected from the group consisting of an ectopic bone formation, osteoporosis, periodontal disease, and osteopetrosis.

The phrase "bone disorder," as used herein, refers to a pathological disorder, disease, or condition in a mammal in which there is an imbalance in the ratio of bone formation to bone resorption, such that, if left untreated, would result in that mammal exhibiting an abnormal mass of bone.

"Treating," "treatment," and "therapy," as used herein, refer to curative, prophylactic, or preventative manipulations, or manipulations which stimulate bone cell differentiation or bone formation, postpone the development of bone disorder symptoms, and/or reduce the severity of bone disorders and/or such symptoms that will or are expected to develop from a bone disorder. The terms further include ameliorating existing bone disorder symptoms, preventing additional symptoms, ameliorating or preventing the underlying metabolic causes of symptoms, preventing or reversing metabolic causes of symptoms, preventing or reversing bone growth, and/or encouraging bone resorption. Thus, the terms denote that a beneficial result has been conferred on a mammal with a bone disorder, or with the potential to develop such disorder.

In another aspect, the invention provides in vivo methods of treating bone disorders in a mammal such as a human, comprising administering to said mammal, a therapeutically effective amount of any of therapeutic compositions of the invention comprising a nucleic acid molecule encoding an osteoactivin protein, or an osteoactivin protein, or biologically active polypeptide fragment thereof, wherein said osteoactivin protein or biologically active polypeptide fragment thereof stimulates bone formation or bone cell differentiation. In other embodiments of this aspect, ex vivo methods for treating bone disorders in a mammal are provided. These methods comprise the steps of: (a) extracting osteoblast cells from said mammal; (b) contacting said osteoblast cells with a therapeutically effective amount of any of the therapeutic compositions comprising a nucleic acid molecule encoding an osteoactivin protein, or biologically active polypeptide fragment thereof, of the invention; and (c) returning said cells to the bone of said mammal, wherein said osteoactivin protein or biologically active polypeptide fragment thereof stimulates bone formation or bone cell differentiation. In certain embodiments, the bone disorder treated is selected from the group consisting of an ectopic bone formation, osteoporosis, periodontal disease, and osteopetrosis. In other certain embodiments of this aspect, the method results in inhibition of bone resorption.

In yet another aspect, the invention provides methods for identifying an agent that modulates the expression or activity of osteoactivin nucleic acid molecules or proteins.

As used herein, an "agent" is a candidate or test compound (e.g., a protein, peptide, peptidomimetic, peptoid, small molecule or other chemical entity) which modulates the expression or activity of the osteoactivin nucleic acid molecule or protein. By "modulating the expression or activity of the osteoactivin nucleic acid molecule or protein" is meant a compound or molecule that has a stimulatory or inhibitory effect on, for example, osteoactivin expression or osteoactivin activity.

The method uses cells capable of expressing a gene under the control of the regulatory element(s) of an osteoactivin gene. Such cells include those which are capable of expressing an endogenous osteoactivin gene (e.g., an osteoblast cell line) or a cell transfected with a transgene comprising an osteoactivin regulatory element (e.g., an osteoactivin promoter) fused to a nucleic acid sequence encoding a polypeptide (e.g., an osteoactivin protein or a reporter protein), such that the osteoactivin gene regulatory element controls expression of the coding sequence.

In a preferred embodiment, the method uses host cells transfected with a nucleic acid comprising an osteoactivin regulatory element fused with nucleic acid sequence encoding a reporter protein. The preferred osteoactivin regulatory element comprises sequences spanning from just upstream of the ATG start site to 8–10 kb upstream of the ATG start site. The method comprises culturing separate samples of cells in the presence and absence of an agent in a suitable culture medium, wherein said cells express a gene under the control of an osteoactivin regulatory element; and measuring and comparing the levels of expression of said gene from said samples of cells cultured in the presence and absence of agent.

In still another aspect, the invention provides assays for determining the presence or absence of a genetic alteration in an osteoactivin polypeptide or in a nucleic acid encoding an osteoactivin protein. One embodiment of the invention is an assay for diagnosing osteopetrosis in a mammal suspected of suffering from osteopetrosis, comprising: (a) measuring the level of osteoactivin protein expression in a biological sample from said mammal; and (b) comparing said level of osteoactivin protein expression to a level of osteoactivin protein expression in a biological sample from a control.

The term "biological sample" includes tissues, cells, and biological fluids isolated from a mammal, as well as tissues, cells and fluids present within a mammal.

In another aspect, a method for diagnosis of osteopetrosis in a mammal is provided. In this method, the level of osteoactivin in the mammal is measured and compared with the level of osteoactivin expressed in a control mammal which does not suffer from osteopetrosis, wherein increased expression in (a) compared to (b) is indicative of osteopetrosis in the mammal in (a).

It is to be understood that the foregoing general description and the following detailed description are exemplary and explanatory, and are intended to provide further explanation of the invention claimed.

BRIEF DESCRIPTION OF THE DRAWINGS

Figures 1A, 1A-1, 1A-2:
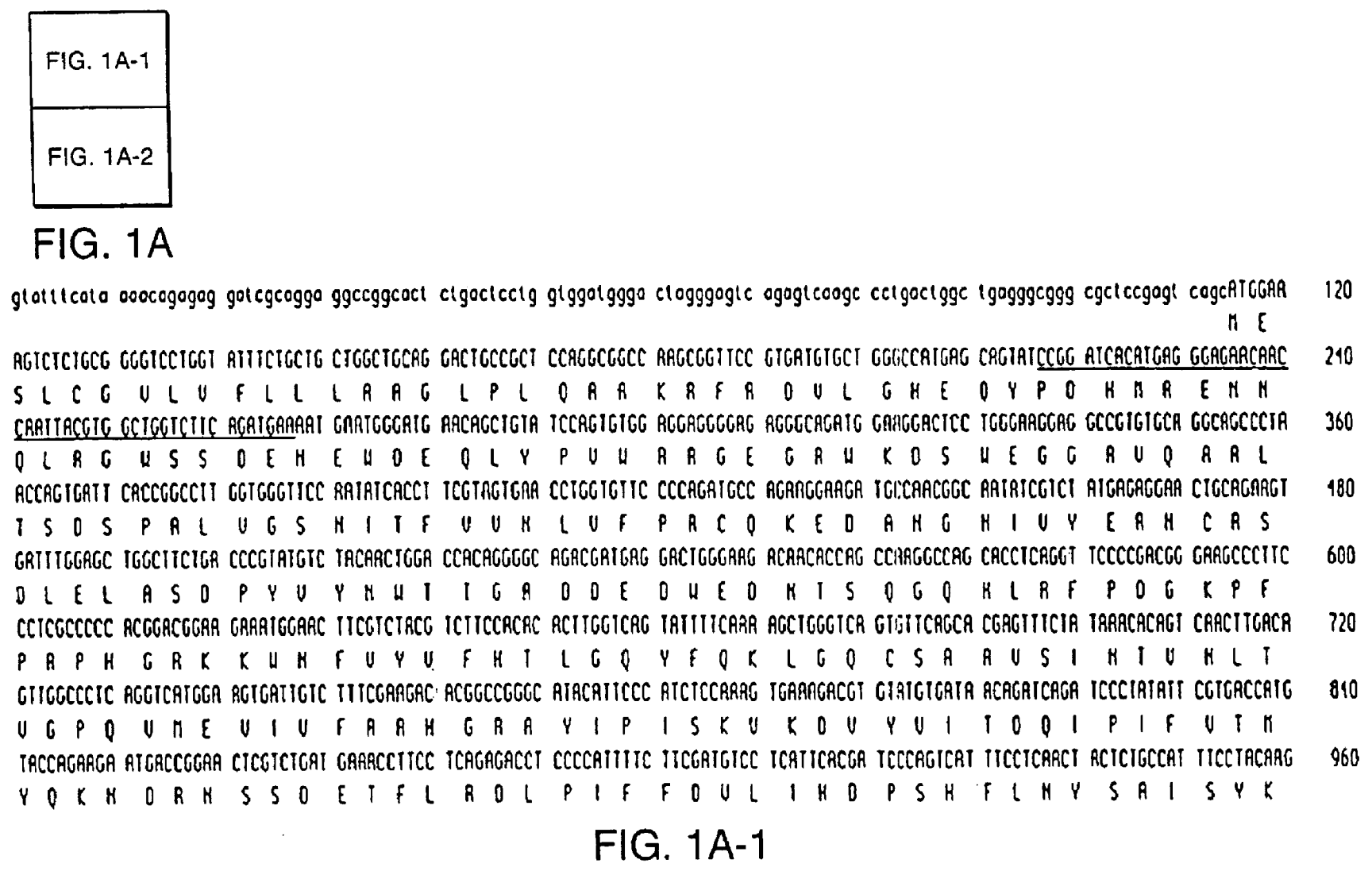
Figure 1A-2:
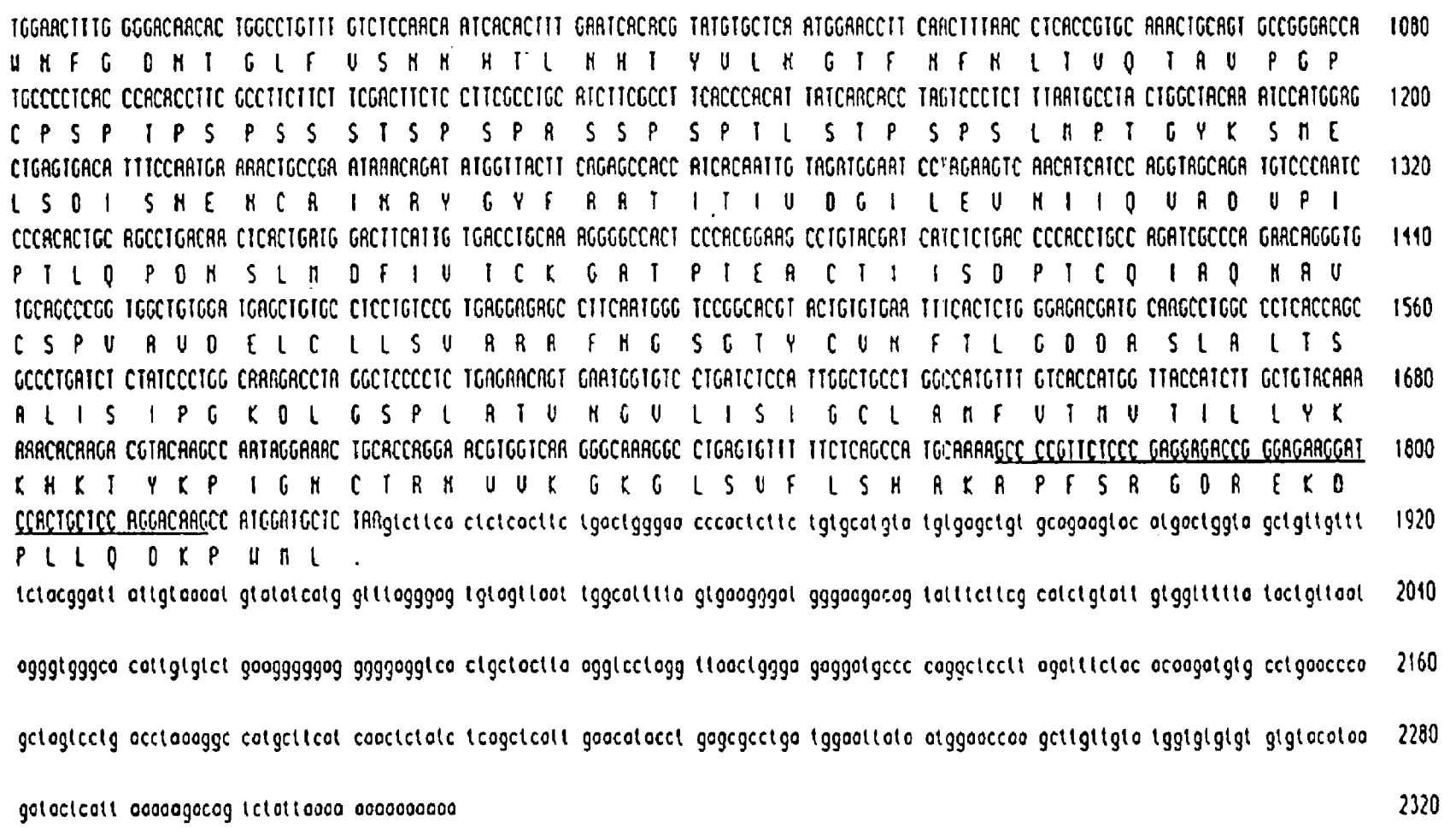

FIG. 1A is a schematic representation of the nucleotide sequence (SEQ ID NO: 1) and corresponding amino acid sequence of rat osteoactivin and its predicted amino acid sequence (SEQ ID NO: 2) (beginning with the methionine at nucleotide 115) shown in single letter format below the DNA sequence. Solid black lines between nucleotides 217 to 267 and 1768 to 1818 underline the peptides to which the antisera were raised for immunohistochemical localization and Western blot analysis of osteoactivin expression.

FIG. 2A is a schematic representation of the alignments of the open reading frame nucleotide sequences of rat osteoactivin (SEQ ID NO: 1), mouse nmb (SEQ ID NO: 7, and human nmb (SEQ ID NO: 8).

FIG. 2B is a schematic representation of the alignment of the predicted amino acid sequences of rat osteoactivin (SEQ ID NO:2), mouse nmb (SEQ ID NO: 5) and human nmb (SEQ ID NO: 6).

FIG. 3 is a representation of an autoradiograph of a differential display gel showing osteoactivin (arrow) in mutant (M) and normal (N) long bone (L) and calvaria (C).

FIG. 4A is a representation of a Northern blot showing osteoactivin expression in the mutant calvaria (M) which was 5-to 7-fold higher than in the normal calvaria (N). Similar results were obtained when RNA from mutant (M) and normal (N) long bone were compared.

FIG. 4B is a representation of the same Northern blot shown in FIG. 4A after stripping and reprobing with a probe for 18s rRNA.

FIG. 5 is a representation showing the immunolocalization of osteoactivin in primary rat osteoblasts, wherein immunofluorescent staining was primarily observed in the perinuclear region of the cell, consistent with localization in the secretory pathways of the cell.

FIG. 5A is a representation of an electron micrograph showing the immunolocalization of osteoactivin in primary rat osteoblasts, wherein immunofluorescent staining was primarily observed in the perinuclear region of the cell, consistent with localization in the secretory pathways of the cell. Primary rat osteoblasts cultured for 5 days were fixed and incubated with chicken anti-osteoactivin primary antibody followed by incubation with a Cy3-conjugated secondary antibody (red). Magnification 175×; insert magnification 350×.

FIG. 5B is a representation of an electron micrograph showing the immunolocalization of the rough endoplasmic reticular (RER) in primary rat osteoblasts. Cells were then stained to visualize the RER using $DiOC_5$ dye (green). Magnification 175×; insert magnification 350×.

FIG. 5C is a representation of an electron micrograph showing the co-localization of immunofluorescent staining of osteoactivin with the immunofluorescent staining of the rough endoplasmic reticulum (RER). Magnification 175×; insert magnification 350×. Images of FIG. 5A and FIG. 5B were overlaid to demonstrate co-localization of staining for osteoactivin with the RER (yellow).

DETAILED DESCRIPTION OF THE INVENTION

Figures 1B, 1C:
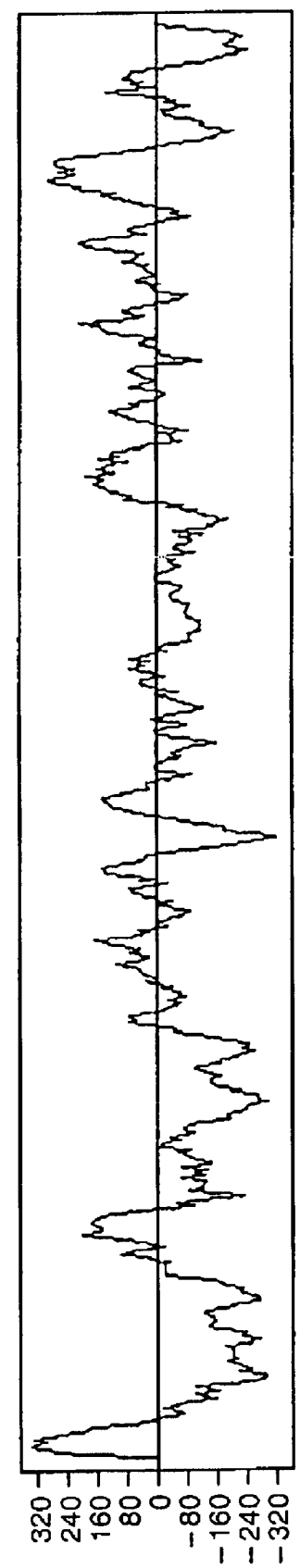
FIG. 1B is a chart characterizing the structure of the human osteoactivin gene from BAC clone RG271G13.
FIG. 1C is a graphic representation of the results of hydropathy analysis of osteoactivin.

The patent applications, patents, and literature references cited herein indicate the knowledge of those of ordinary skill in this field and are hereby incorporated by reference in their entirety. In the case of inconsistencies between any reference cited herein and the specific teachings of the present disclosure, this disclosure will prevail. Similarly, any inconsistencies between an art-understood meaning of a term and a meaning of a term as specifically taught in the present disclosure will be resolved in favor of this disclosure.

The present invention discloses a cDNA encoding a novel protein, osteoactivin, first identified in the bone of rats carrying the op mutation. A comparison of gene expression in normal versus op long bones and calvaria using mRNA-differential display resulted in the identification and cloning of a cDNA encoding the osteoactivin protein. Osteoactivin mRNA is highly over-expressed in op versus normal bone. These findings provide evidence that the protein encoded by this cDNA plays a role in osteoblast development, bone cell differentiation, and bone formation, and therefore, is involved in normal skeletal modeling/remodeling.

Nucleic Acid Molecules Encoding an Osteoactivin Protein

The rat full-length osteoactivin nucleic acid sequence (FIG. 1A; SEQ ID NO:1), which is approximately 2320 nucleotides long including untranslated regions, contains a predicted methionine-initiated coding sequence of 1716 nucleotides (nucleotides 115–1830 of SEQ ID NO:1). This full-length nucleic acid sequence has been deposited in GenBank and has Accession Number AF184983.

Figures 2A, 2A-1, 2A-2, 2A-3, 2A-4, 2A-5:
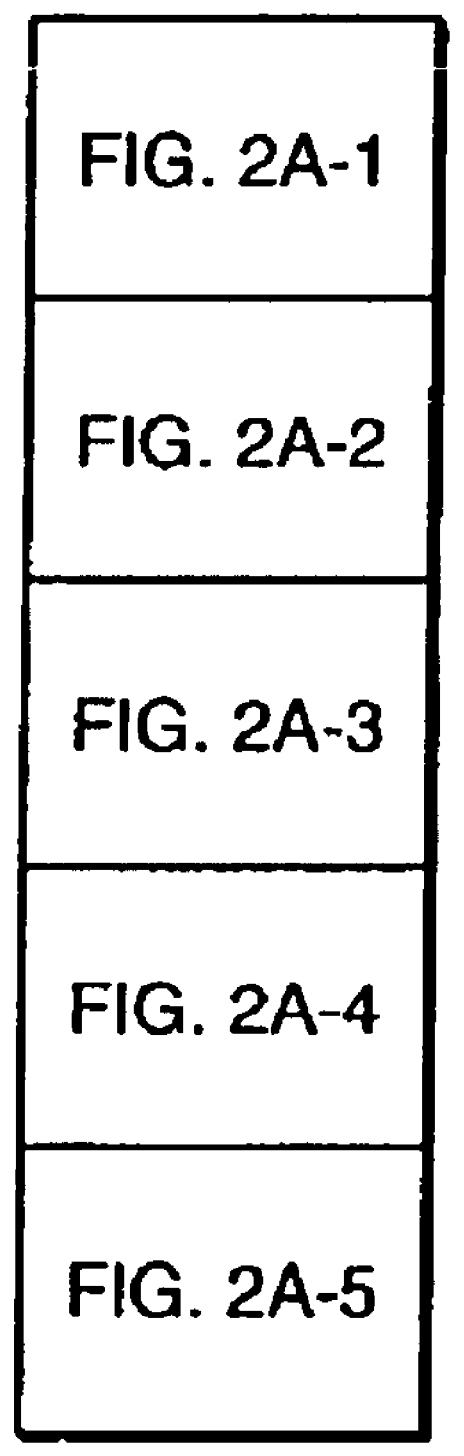

A GenBank search identified human and mouse nmb proteins found in melanoma cell lines that are likely homologs of the rat osteoactivin protein disclosed herein (Waterman et al., *Int. J. Cancer* 60:73–81 (1995); Bachner et al., GenBank Accession No. AJ 251685). A comparison of the nucleotide sequences of the open reading frames of the rat osteoactivin, human nmb, and mouse nmb, genes is shown in FIG. 2A. Of the 1716 nucleotides in the rat osteoactivin coding region, 1304 nucleotides were identical in human, which corresponds to 76% sequence identity. Of the 1716 nucleotides in the rat osteoactivin coding region, 1574 nucleotides were identical in mouse, which corresponds to 91% sequence identity.

To determine the percent sequence identity of two amino acid sequences, or of two nucleic acid sequences, the sequences were aligned for optimal comparison purposes (e.g., gaps can be introduced in one or both of a first and a second amino acid or nucleic acid sequence for optimal alignment and non-homologous sequences can be disregarded for comparison purposes). Preferably, the length of a reference sequence aligned for comparison purposes is at least 30%, more preferably at least 40%, even more preferably at least 50%, even more preferably at least 60%, and even more preferably at least 70% of the length of the reference sequence. The amino acid residues or nucleotides at corresponding amino acid positions or nucleotide positions were then compared. When a position in the first sequence was occupied by the same amino acid residue or nucleotide as the corresponding position in the second sequence, the molecules were considered identical at that position. The percent sequence identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. For example, the percent sequence identity between two amino acid sequences is determined using the Needleman and Wunsch algorithm (*J. Mol. Biol.* 48:444–453 (1970)) which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. Alternatively, the percent sequence identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain what parameters should be applied to determine if a molecule is within a sequence identity or homology limitation of the invention) are a Blossum 62 scoring matrix with a gap penalty of 12, a gap extend penalty of 4, and a frameshift gap penalty of 5. The percent sequence identity between two amino acid or nucleotide sequences can also be determined using the algorithm of E. Meyers and W. Miller (*CABIOS*, 4:11–17 (1989)) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul et al. (*J. Mol. Biol.* 215:403–10 (1990)). BLAST nucleotide searches can be performed with the NBLAST program, score=100, wordlength=12 to obtain nucleotide sequences homologous to osteoactivin nucleic acid molecules of the invention. BLAST protein searches can be performed with the XBLAST program, score=50, wordlength=3 to obtain amino acid sequences homologous to osteoactivin protein molecules of the invention. To obtain gapped alignments for comparison purposes, Gapped BLAST can be utilized as described in Altschul et al. (*Nucleic Acids Res.* 25(17):3389–3402 (1997)). When utilizing BLAST and Gapped BLAST programs, the default parameters of the respective programs (e.g., XBLAST and NBLAST) can be used (see, http://www.ncbi.nlm.nih.gov).

A GenBank search using the rat osteoactivin cDNA as the query identified the presence of the human osteoactivin gene on BAC clone RG27G13. Alignment of the human osteoactivin /nmb cDNA sequence with this BAC clone demonstrates that the human osteoactivin transcript is encoded by 11 exons spanning 28.3 kb, as shown in FIG. 1B. These exons range in size from 95 bp to 1019 bp. Southern blot analysis indicates that osteoactivin is a single copy gene in the human genome. FISH analysis, radiation hybrid mapping, and bioinformatic localization all place the human osteoactivin gene on chromosome 7p15.1. No other genes involved in bone metabolism have been reported at this locus. 5' RACE analysis of human osteoactivin in both human osteoblasts and kidney mRNA demonstrate that the same transcriptional initiation site was used in both tissues and that this site mapped to the end of the human nmb cDNA as previously reported. Osteoactivin is expressed in human osteoblasts in culture as a single transcript of approximately 2.4 kb.

The invention further contemplates nucleic acid molecules that differ from the nucleotide sequence shown in SEQ ID NO:1, or the nucleotide sequence of the DNA insert of the plasmid deposited with GenBank as Accession Number AF184983. Such differences can be due to degeneracy of the genetic code, and result in a nucleic acid which encodes the same osteoactivin proteins as those encoded by the nucleotide sequence disclosed herein. The invention provides an isolated nucleic acid molecule encoding a protein having an amino acid sequence which differs by at least 1, but by less than 5, 10, 20, 50, or 100 amino acid residues than shown in SEQ ID NO:2. If alignment is needed for this comparison, the sequences should be aligned for maximum homology. "Looped" out sequences from deletions or insertions, or mismatches, are considered differences.

Nucleic acid molecules of the invention can be chosen for having codons which are preferred or non-preferred for a particular expression system. For example, the nucleic acid can be one in which at least one codon, and preferably at least 10%, or 20% of the codons, have been altered such that the sequence is optimized for expression in, e.g., E. coli, yeast, human, insect, or Chinese hamster ovary (CHO) cells.

Nucleic acid variants can be naturally occurring, such as allelic variants (same locus), homologs (different locus), and orthologs (different organism), or can be non-naturally occurring. Non-naturally occurring variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product), as described below.

Preferably, the nucleic acid sequence differs from that of SEQ ID NO:1, or the sequence in GenBank Accession Number AF184983, e.g., by at least one nucleotide but less than 10, 20, 30, or 40 nucleotides. Alternatively, the nucleic acid sequence differs from that of SEQ ID NO:1 or of AF18493 by at least one but less than 1%, 5%, 10% or 20% of the nucleotides in the subject nucleic acid. If necessary for this analysis the sequences should be aligned for maximum homology. "Looped" out sequences from deletions or insertions, or mismatches, are considered differences.

SignalP analysis (CBS SignalP V1.1 World Wide Web Prediction Server at the Center for Biological Sequence (http://www.cbs.dtu.dk)) was used to analyze the sequence of osteoactivin for the presence of a signal peptide. Signal P calculates the maximal C-(raw cleavage site score), S-(signal peptide score), and Y-(combined cleavage site score) scores, and the mean S-score, between the N-terminal and the predicted cleavage site. SignalP analysis of osteoactivin revealed a mean S score of 0.907, indicating that osteoactivin has a signal sequence. The cleavage site for the signal peptide was predicted to occur between residues 22 and 23 of rat osteoactivin (SEQ ID NO:2). This region is conserved across species, indicating that mouse and human osteoactivin contain the same leader sequence and cleavage site. Accordingly, osteoactivin polypeptides lacking the signal sequence are functionally active osteoactivin polypeptides.

The invention, therefore, provides for nucleic acid molecules encoding the osteoactivin polypeptide lacking the signal sequence, wherein the osteoactivin polypeptide comprises amino acid residues 23–572 of SEQ ID NO:2. This nucleic acid molecule encoding the osteoactivin protein lacking the signal sequences comprises the nucleic acid sequence of nucleotides 181–1830 of SEQ ID NO:1.

Orthologs, homologs, and allelic variants can be identified using methods known in the art. These variants comprise a nucleotide sequence encoding a polypeptide that is 50%, at least 55%, typically at least 70–75%, more typically at least 80–85%, and most typically at least 90–95% or more identical to the nucleotide sequence shown in SEQ ID NO:1 or to a fragment of this sequence. Such nucleic acid molecules can readily be identified as being able to hybridize under moderately stringent conditions to the nucleotide sequence shown in SEQ ID NO:1, or a fragment of the sequence. Nucleic acid molecules corresponding to orthologs, homologs, and allelic variants of the osteoactivin cDNAs of the invention can further be isolated by mapping to the same chromosome or locus as the osteoactivin gene. Preferred variants are those that maintain their biological function including the ability to bind osteoactivin binding partners.

An "allelic variant," as used herein, is a protein having at least 75% identity, preferably at least 85%, more preferably at least 95%, and most preferably at least 99% identity to the amino acid sequence of osteoactivin, or to a fragment thereof, or to a protein conjugate thereof which retains the biological activity of osteoactivin. Allelic variants of osteoactivin include both functional and non-functional proteins. Functional allelic variants are naturally occurring amino acid sequence variants of the osteoactivin protein within a population that maintain their biological function including the ability to bind osteoactivin binding partners. Functional allelic variants will typically contain only conservative substitution(s) of one or more amino acids of SEQ ID NO:2, or the substitution, deletion or insertion of non-critical residues in non-critical regions of the protein. Non-functional allelic variants are naturally-occurring amino acid sequence variants of the osteoactivin protein, e.g., human osteoactivin protein, within a population that does not have osteoactivin biological activity such as the ability to bind osteoactivin binding partners. Non-functional allelic variants will typically contain a non-conservative substitution, a deletion or insertion, or premature truncation of the amino acid sequence of SEQ ID NO:2, or a substitution, insertion, or deletion in critical residues or critical regions of the protein.

Osteoactivin Proteins and Polypeptide Fragments

The nucleotide coding sequence encodes a 572 amino acid protein shown in FIG. 1A (SEQ ID NO:2). The protein has a predicted molecular weight of 63.8 kD. Hydropathy analysis, shown in FIG. 1C, reveals a potential leader sequence with a cleavage site after amino acid residue 22 in SEQ ID NO:2, as well as several potential transmembrane spanning regions throughout the molecule.

FIG. 2B shows the amino acid sequences of rat osteoactivin, human nmb, and mouse nmb, aligned to determine the percentage of sequence identity. Of the 572 amino acid residues in the rat osteoactivin protein, 394 amino acid residues were identical in human, which corresponds to 69% sequence identity. Notably, the predicted protein sequence of the rat osteoactivin has a proline/serine-rich 14 amino acid residue insertion beginning at amino acid residue 33 that is not present in the human nmb homolog. Of the 572 amino acid residues in the rat osteoactivin protein, 509 amino acid residues were identical to mouse, which corresponds to 89% sequence identity.

An osteoactivin protein of the invention is a protein which comprises the amino acid sequence of SEQ ID NO:2, SEQ ID NO:5 or SEQ ID NO:6, and alternatively or additionally, comprises an osteoactivin protein having at least 90% sequence identity to the amino acid sequence of SEQ ID NO:2, SEQ ID NO:5 or SEQ ID NO:6 and stimulates bone cell differentiation or bone formation. An osteoactivin protein of the invention further comprises the osteoactivin protein sequence lacking the signal sequence comprising amino acid residues 23–572 of SEQ ID NO:2.

The osteoactivin proteins, polypeptide fragments thereof, mutants, truncations, derivatives, and splice variants of SEQ ID NO:2 that display substantially equivalent or altered osteoactivin activity relative to SEQ ID NO:2 are likewise contemplated. These variants may be deliberate, for example, such as modifications obtained through site-directed mutagenesis, or may be accidental, such as those obtained through mutations in hosts that are producers of the osteoactivin protein. Included within the scope of these terms are osteoactivin proteins specifically recited herein, as well as all substantially homologous analogs and allelic variants.

Analogs may be made through substitution of conserved amino acids. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an osteoactivin protein is preferably replaced with another amino acid residue from the same side chain family. Alternatively, in another embodiment, mutations can be introduced randomly along all or part of an osteoactivin coding sequence, such as by saturation mutagenesis, and the resultant mutants can be screened for osteoactivin biological activity to identify mutants that retain activity. Following mutagenesis of SEQ ID NO:1, or the nucleotide sequence of the DNA insert of the plasmid deposited with GenBank as Accession Number AF184983, the encoded protein can be expressed recombinantly and the activity of the protein can be determined.

A "non-essential" amino acid residue is a residue that can be altered from the wild-type sequence of osteoactivin (e.g., the sequence of SEQ ID NO:1, or the nucleotide sequence of the DNA insert of the plasmid deposited with GenBank as Accession Number AF184983) without abolishing or, more preferably, without substantially altering a biological activity, whereas an "essential" amino acid residue results in such a change. For example, amino acid residues that are conserved among the polypeptides of the present invention are predicted to be particularly unamenable to alteration.

As used herein, a "biologically active portion" of an osteoactivin protein includes a fragment of an osteoactivin protein that can modulate bone cell differentiation or stimulate bone formation. Biologically active portions of an osteoactivin protein include peptides comprising amino acid sequences sufficiently homologous to or derived from the amino acid sequence of an osteoactivin protein, e.g., the amino acid sequence shown in SEQ ID NO:2, which include less amino acids than a full length osteoactivin proteins and which exhibit at least one activity of an osteoactivin protein. A biologically active portion of an osteoactivin protein can be a polypeptide which is, e.g., 10, 25, 50, 100, 200 or more amino acids in length. Biologically active portions of an osteoactivin protein can be used as targets for developing agents which modulate an osteoactivin-mediated activity.

Because osteoactivin proteins of this invention modulate bone cell differentiation and bone formation, they are useful for developing novel therapeutic compositions for bone disorders, as described in more detail below.

Vectors

Preferably, a biologically functional expression vector of the invention includes one or more regulatory sequences operatively linked to the nucleic acid sequence to be expressed. The term "regulatory sequence" includes promoters, enhancers, and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors of the invention can be introduced into host cells to thereby produce proteins or polypeptides, including fusion proteins or polypeptides, encoded by nucleic acids as described herein (e.g., osteoactivin proteins, mutant forms of osteoactivin proteins, fusion proteins, and the like).

The biologically functional recombinant expression vectors of the invention can be designed for expression of osteoactivin proteins in prokaryotic or eukaryotic cells. For example, representative osteoactivin expression vectors are yeast expression vectors and vectors for expression in insect cells (e.g., a baculovirus expression vector) or a vector suitable for expression in mammalian cells such as yeast or CHO cells. Alternatively, the recombinant expression vector can be transcribed and translated in vitro, for example, using T7 promoter regulatory sequences and T7 polymerase. Suitable host cells are discussed further in Goeddel (*Meth. Enzymol.* 185:3–7 (1990)).

For example, expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes and their cognate recognition sequences include, but are not limited to, Factor Xa, thrombin and enterokinase. Typical fusion expression vectors include pGEX (Amersham Pharmacia Biotech Inc., Piscataway, N.J.; Smith et al., *Gene* 67:31–40 (1988)), and pMAL (New England Biolabs, Beverly, Mass.) which fuse glutathione S-transferase (GST), maltose E binding protein, or protein A to the target recombinant protein.

Purified fusion proteins can be used in osteoactivin activity assays, (e.g., direct assays or competitive assays described in detail below), or to generate antibodies specific for osteoactivin proteins. In one non-limiting example, a retroviral expression vector encoding a fusion protein can be used to infect bone marrow cells which are subsequently transplanted into irradiated recipients. The pathology of the subject recipient is then examined after sufficient time has passed (e.g., six weeks).

To maximize recombinant protein expression in *E. coli*, the protein can be expressed in a host bacteria with an impaired capacity to proteolytically cleave the recombinant protein (Gottesman, S., *Meth. Enzymol.* 185:119–128, (1990)). Another strategy is to alter the nucleotide sequence of the nucleic acid to be inserted into an expression vector so that the individual codons for each amino acid are those preferentially utilized in *E. coli* (Wada et al., *Nucleic Acids Res.* 20:2111–2118 (1992)). Such alteration of nucleic acid sequences of the invention can be carried out by standard DNA synthesis techniques.

When used in mammalian cells, the control functions of the expression vector are often provided by viral regulatory elements. For example, commonly used promoters are derived from polyoma, Adenovirus 2, cytomegalovirus, or Simian Virus 40.

Antibodies

The present invention also encompasses antibodies that recognize and bind to the osteoactivin protein or fragment thereof (e.g., to one or more epitopes of the protein having SEQ ID NOS:2 or 6). These antibodies are polyclonal or monoclonal antibodies which may be provided using standard methods (see, e.g., Ausubel et al., supra; Coligan, J. E. et al., *Current Protocols in Immunology*, John Wiley & Sons, New York (1991); and Delves, P. J., *Antibody Production: Essential Techniques*, John Wiley & Sons, New York (1997)). Briefly, osteoactivin protein or a polypeptide fragment purified according to the methods described for an aspect of the invention are used to immunize rabbits (e.g., for polyclonal antibodies) or mice (e.g., for monoclonal antibodies) to generate antibody-mediated immunity to the osteoactivin protein or polypeptide fragment used to immunize the animal. Monoclonal antibodies can be screened by, e.g., ELISA, to identify those that show the highest affinity for the immunizing osteoactivin protein or polypeptide fragment. The cloned cell producing the high affinity monoclonal antibody can then be propagated in vitro (where the antibody is purified from the culture supernatant) or in vivo (where the antibody is purified from ascites fluid), and can also be cryopreserved and stored frozen, e.g., at −70° C. in DMSO, to provide a potentially limitless supply of monoclonal antibody. Antibodies can also be provided by known recombinant DNA techniques.

In addition to intact monoclonal and polyclonal antibodies, the invention also provides various fragments of an osteoactivin antibody, such as Fab, F(ab')$_2$, Fv, and sFv fragments, which can be produced by proteolytic cleavage or recombinant DNA techniques. Humanized antibodies are also provided and can be produced according to methods known in the art (see, e.g., Green et al., *Nature Genetics* 7:13–21 (1994)).

Also provided by the invention are osteoactivin protein-specific single polypeptide chain antibodies (see general methods in U.S. Pat. Nos. 4,946,788 and 4,704,692); single domain antibodies (see, e.g., Ward et al., *Nature* 341:544–546 (1989)); and chimeric antibodies (see, e.g., U.S. Pat. No. 4,816,567). A single-chain antibody (scFV) may be engineered by known methods (see, e.g., Colcher et al., *Ann. NY Acad. Sci.* 880:263–80 (1999); and Reiter, *Clin. Cancer Res.* 2:245–52 (1996)). The single chain antibody can be dimerized or multimerized to generate multivalent antibodies having specificities for different epitopes of the same target osteoactivin protein.

Preferably, the antibody of the invention specifically binds to its specific ligand with a dissociation constant ($K_D$) of at least $10^{-5}$ M, more preferably, of at least $10^{-6}$ M, even more preferably, of at least $10^{-7}$ M, and most preferably, with a $K_D$ of at least $10^{-8}$ M.

Antibodies that specifically bind osteoactivin protein or polypeptide fragments thereof are useful, for example, in determining expression levels of osteoactivin protein in various tissues of the body, in Western blotting analysis, and in immunochromatography.

A full-length osteoactivin protein or an antigenic peptide fragment of osteoactivin can be used as an immunogen or can be used to identify anti-osteoactivin antibodies made with other immunogens (e.g., cells, membrane preparations, and the like). The antigenic peptide of osteoactivin preferably includes at least eight sequential amino acid residues from SEQ ID NO:2 and encompasses an epitope of osteoactivin. Preferably, the antigenic peptide includes at least 10 amino acid residues, more preferably at least 15 amino acid residues, even more preferably at least 20 amino acid residues, and most preferably at least 30 amino acid residues.

Fragments of the osteoactivin amino acid residues 35–51 (SEQ ID NO:3; hereinafter "peptide 35") or amino acid residues 551–568 (SEQ ID NO:4; hereinafter "peptide 551"), or amino acid residues 538–553 of SEQ ID NO:6 can be used, e.g., as immunogens to make or characterize the specificity of an antibody against osteoactivin protein. Antibodies reactive with, or specific for, any of these regions of osteoactivin, or other regions or domains described herein are provided.

Exemplary preferred epitopes encompassed by the antigenic peptide are regions of osteoactivin located on the surface of the protein, e.g., hydrophilic regions. For example, an Emini surface probability analysis of the human osteoactivin protein sequence can be used to indicate the regions that have a particularly high probability of being localized to the surface of the osteoactivin protein, and are thus likely to constitute surface residues useful for targeting antibody production. However, antibodies of the invention bind an epitope on any domain or region on osteoactivin proteins described herein.

Chimeric, humanized, but most preferably, completely human antibodies are desirable for applications which include repeated administration, e.g., therapeutic treatment (and some diagnostic applications) of human patients.

Some antibodies of the invention have a reduced ability or no ability to bind an Fc receptor, for example, where it is an isotype or subtype, fragment, or other mutant, which does not support binding to an Fc receptor, or where it has a mutagenized or deleted Fc receptor binding region.

An anti-osteoactivin antibody (e.g., monoclonal antibody) can be used to isolate osteoactivin by standard techniques, such as by affinity chromatography or immunoprecipitation. Moreover, an anti-osteoactivin antibody can be used to detect osteoactivin protein (e.g., in a cellular lysate or cell supernatant) in order to evaluate the abundance and pattern of expression of the protein. Anti-osteoactivin antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Non-limiting examples of detectable substances include various enzymes, prosthetic groups, fluorescent materials, luminescent materials, bioluminescent materials, and radioactive materials. Non-limiting examples of suitable enzyme labels include horseradish peroxidase, alkaline phosphatase, galactosidase, and acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride, and phycoerythrin. An example of a luminescent material includes, but is not limited to, luminol. Non-limiting examples of bioluminescent materials include luciferase, luciferin, and aequorin. Non-limiting examples of suitable radioactive material include $^{125}$I, $^{131}$I, $^{35}$S, and $^{3}$H. Coupling of labels to antibodies can be accomplished using standard techniques (see, e.g., *Antibodies, A Laboratory Manual*, Hanlos and Lane, eds. Cold Spring Harbor Laboratory Press, Cold Spring Harbor, N.Y., 1999).

Therapeutic Compositions

The osteoactivin-encoding nucleic acid and osteoactivin polypeptides and fragments thereof, as well as anti-osteoactivin antibodies (also collectively referred to herein as "active compounds"), of the invention, or an agent that modulates osteoactivin activity or expression, can be incorporated into therapeutic compositions. Such compositions typically include osteoactivin nucleic acid molecules, proteins, antibodies, or agents and preferably includes a pharmaceutically acceptable delivery vehicle or carrier. As used herein the language "pharmaceutically acceptable delivery vehicle" includes solvents, dispersion media, coatings, antibacterial and antifungal agents, isotonic and absorption delaying agents, and the like, compatible with pharmaceutical administration. This delivery vehicle may be targeted to the bone or bone cells by virtue of its composition, for example, using a bisphosphanate tetracycline, or calcein. Alternatively, a vehicle may be a polymer or collagen composition that is applied to bone during surgery or by injection at the bone site (see, e.g. U.S. Pat. Nos. 4,938,763; 5,278,201; 5,324,519; 5,487,897; 5,599,552; 5,702,716; 5,733,950; 5,739,176; 5,744,153; 5,759,563; 5,780,044; 5,945,115; 5,990,194; and 5,631,243). Additional active compounds can also be incorporated into the compositions.

A therapeutic composition is formulated to be compatible with its intended route of administration. Non-limiting examples of routes of administration include parenteral, e.g., intravenous, intradermal, subcutaneous, oral (e.g., by ingestion or inhalation), transdermal (topical), transmucosal, and rectal administration. Oral administration or injection at a bone site is preferred. Solutions or suspensions can be made as described in *Remington's Pharmaceutical Sciences*, (18$^{th}$ ed., Gennaro, ed., Mack Publishing Co., Easton, Pa., (1990)).

Therapeutic efficacy of such active compounds can be determined by standard therapeutic procedures in cell cultures or experimental animals, e.g., for determining the ED50 (the dose therapeutically effective in 50% of the population).

The data obtained from the cell culture assays and animal studies can be used in formulating a range of dosage for use in humans. The dosage may vary depending upon the dosage form employed and the route of administration. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from 0.001 to 30 mg/kg body weight, preferably 0.01 to 25 mg/kg body weight, more preferably 0.1 to 20 mg/kg body weight, and even more preferably 1 to 10 mg/kg, 2 to 9 mg/kg, 3 to 8 mg/kg, 4 to 7 mg/kg, or 5 to 6 mg/kg body weight. The protein or polypeptide can be administered one time per week for between 1 to 10 weeks, preferably between 2 to 8 weeks, more preferably between 3 to 7 weeks, and even more preferably for 4, 5, or 6 weeks. The skilled artisan will appreciate that certain factors may influence the dosage and timing required to effectively treat a mammal including, but not limited to, the severity of the disease or disorder, previous treatments, the general health and/or age of the mammal, and other diseases present. Moreover, treatment of a mammal with a therapeutically effective amount of an osteoactivin protein, polypeptide, or antibody can include a single treatment or, preferably, can include a series of treatments.

For antibodies, the preferred dosage is generally 10 mg/kg to 20 mg/kg body weight. Generally, partially humanized antibodies and fully human antibodies have a longer half-life within the human body than other antibodies. Accordingly, lower dosages and less frequent administration are possible. Modifications such as lipidation can be used to stabilize antibodies and to enhance uptake and tissue penetration (e.g., into the brain). A method for lipidation of antibodies is described in Cruikshank et al. (*J. Acquired Immune Deficiency Syndromes Hum. Retrovirol.* 14:193 (1997)).

The therapeutic compositions may also include other active or inert components. Of particular interest are those mediators that promote bone growth or infiltration, such as cytokines and growth factors. Non-limiting exemplary mediators for this purpose include interleukin-1, tumor necrosis factor, lymphotoxin, interleukin-6, prostaglandins of the E-series, leukotrienes, lipopolysaccharides, transforming growth factor-β, and colony-stimulating factors. Agents that promote bone growth, such as bone morphogenic proteins, are also useful.

Within the present invention, a "therapeutically effective amount" of a therapeutic composition is that amount which produces a desired effect. For example, a therapeutically effective amount is the amount of the therapeutic composition comprising the active osteoactivin protein compound herein required to provide an effect in reversing the symptoms of the bone disorder. Such therapeutically effective amounts will be determined using routine optimization techniques that are dependent on the particular condition to be treated, the condition of the patient, the route of administration, the formulation, and the judgment of the practitioner and other factors evident to those skilled in the art. The dosage required for the therapeutic compositions of the invention, for example, in osteoporosis where an increase in bone formation is desired, is manifested as a statistically significant difference in bone mass between treatment and control groups. Other measurements of increases in bone formation and/or bone healing may include, for example, tests for breaking strength and tension, breaking strength and torsion, 4-point bending, increased connectivity in bone biopsies and other biomechanical tests well known to those skilled in the art. General guidance for treatment regimens is obtained from experiments carried out in animal models.

Therapeutic Methods

The therapeutic compositions of the present invention may be used to modulate the differentiation of osteoblasts, osteoblast precursors, and mesenchymal cells in vivo, in vitro, or ex vivo, and to modulate bone cell differentiation and bone formation. As used herein, the term "osteoblast precursor" refers to a cell that is committed to a differentiation pathway, but that generally does not express markers or function as a mature, fully differentiated cell. Such cells include "mesenchymal cells" or "mesenchymal stem cells," which are pluripotent cells that are capable of dividing many times and whose progeny will give rise to skeletal tissues, including cartilage, bone (osteogenic cells), tendon, ligament, marrow stroma and connective tissue. The disclosed therapeutic compositions or methods are useful for stimulating osteogenesis.

In a preferred method, bone cell differentiation and bone formation is stimulated by administering to a mammal a therapeutic composition comprising a nucleic acid molecule encoding an osteoactivin protein, or comprising an osteoactivin protein or biologically active polypeptide fragment thereof, or comprising an agent that stimulates osteoactivin expression or activity. The appropriate agent can be determined based on screening assays described herein. Bone disorders in mammals that may be treated or prevented by administering one of the above-described therapeutic compositions of the invention include those diseases or pathological conditions in which stimulation of bone cell formation is desired, such as with osteoporosis or bone trauma.

As an alternative, bone cell differentiation and bone formation can be inhibited by administering to a mammal a therapeutic composition comprising an osteoactivin antibody, an osteoactivin antisense nucleic acid, or an agent that inhibits osteoactivin expression or activity. Such therapy is used in treating, for example, osteopetrosis. Examples of osteoactivin antibodies include, for example, polyclonal, monoclonal, humanized, anti-idiotypic, chimeric or single chain antibodies, and Fab, F(ab')$_2$ and Fab expression library fragments, scFV molecules, and epitope-binding fragments thereof. An antisense oligonucleotide directed to the osteoactivin gene or mRNA to inhibit its expression is made according to standard techniques. (See, e.g., Agrawal et al. *Methods in Molecular Biology: Protocols for Oligonucelotides and Analogs*, Vol. 20 (1993)). An agent that inhibits osteoactivin activity or expression is identified by screening assays, as described herein.

In another preferred method, hematopoietic osteogenic cells are removed ex vivo from the cell population, either before or after contact or stimulation with a disclosed therapeutic composition. Through well-known practices, the osteogenic cells may be expanded. The expanded osteogenic cells can be infused or reinfused into a mammal in need thereof.

Screening Methods

The invention provides methods (also referred to herein as screening assays") for identifying modulators of osteoactivin expression and or osteoactivin activity. Such modulators (i.e., candidates, test compounds, agents, proteins, peptides, peptidomimetics, peptoids, small molecules or other chemical entities) stimulate or inhibit osteoactivin expression or activity. Therefore, agents thus identified can be used to regulate bone cell differentiation and bone formation in a therapeutic protocol.

The test compounds used for screening may be selected individually or obtained from a compound library. Such libraries include biological libraries, peptoid libraries (libraries of molecules having the functionalities of peptides, but with a novel, non-peptide backbone which are resistant to enzymatic degradation but which nevertheless remain bioactive) (see, e.g., Zuckermann, *J. Med. Chem.* 37:2678–85 (1994)), spatially addressable parallel solid phase or solution phase libraries, synthetic library methods requiring deconvolution, the "one-bead one-compound" library method, and synthetic library methods using affinity chromatography selection. The biological library and peptoid library approaches are limited to peptide libraries, while the other four approaches are applicable to peptide, non-peptide oligomer or small molecule libraries of compounds (Lam, *Anticancer Drug Dis.* 12:145 (1997)).

Examples of methods for the synthesis of molecular libraries can be found in the art, for example, in: DeWitt et al., *Proc. Natl. Acad. Sci. (USA)* 90:6909 (1993); Erb et al., *Proc. Natl. Acad. Sci. (USA)* 91:11422 (1994); Zuckermann et al., *J. Med. Chem.*, 37:2678 (1994); Cho et al., *Science*, 261:1303 (1995); Carrell et al., *Angew. Chem. Int. Ed. Engl.* 33:2059 (1994); Carell et al., *Angew. Chem. Int. Ed. Engl.* 33:2061 (1994); and in Gallop et al., *J. Med. Chem.* 37:1233 (1994).

Libraries of compounds may be presented in solution (e.g., Houghten, *Biotechniques*, 13:412–421 (1992)), or on beads (Lam, *Nature* 354:82–841 (1991)), on chips (Fodor, *Nature* 364:555–556 (1993)), bacteria (Ladner U.S. Pat. No. 5,223,409), spores (Ladner U.S. Pat. No. 5,223,409), plasmids (Cull et al., *Proc. Natl. Acad. Sci. USA.*, 89:1865–1869 (1992)) or on phage (Scott et al., *Science* 249:386–390 (1990); Devlin, *Science* 249:404–406 (1990); Cwirla et al., *Proc. Natl. Acad. Sci. (USA)* 87:6378–6382 (1990); Felici, *J. Mol. Biol.* 222:301–310 (1991); Ladner supra.).

In one embodiment, the invention provides an assay for identifying an agent that modulates the expression of an osteoactivin protein. The method uses cells capable of expressing a gene under the control of the regulatory element(s) of an osteoactivin gene. Such cells include those which are capable of expressing an endogenous osteoactivin gene (e.g., an osteoblast cell line) or a cell transfected with a transgene comprising an osteoactivin regulatory element (e.g., an osteoactivin promoter) fused to a nucleic acid sequence encoding a polypeptide (e.g., an osteoactivin protein or a reporter protein), such that the osteoactivin gene regulatory element controls expression of the coding sequence.

In a preferred embodiment, the human osteoactivin gene promoter is used to identify agents that modulate osteoactivin gene expression. The sequence of the human osteoactivin promoter can be found in clone RG271G13 from the Genome Sequencing Center (Washington Univ., St. Louis, Mo.) (GenBank Accession Number AC005082) which encodes the human osteoactivin gene and promoter. The initiation of translation (ATG) starts at bp 86355 of this clone and a probable TTATAA box starts at bp 86510. A portion of this promoter, preferably 8–10 kb upstream of the ATG start site, is cloned into a vector containing, for example, a reporter gene (such as secreted alkaline phosphatase, green fluorescent protein, or luciferase) and a gene encoding antibiotic resistance. The vector is transfected into an osteoblastic cell line, such as, e.g., MG-63, HO5, or SaOS, (all available from the American Type Culture Collection, Manassas, Va.) which expresses an endogenous osteoactivin gene. Following transfection, cells that incorporate the construct are selected by their ability to grow in the presence of an appropriate antibiotic and, subsequently, clonal cell lines are established by limiting dilution.

The expression of the reporter gene in these cell lines is determined by the appropriate measurement of reporter gene expression. Expression is measured at confluence and compared to an appropriate control cell line, such as a cell line transfected with a construct in which the promoter was cloned in the opposite orientation, in a cell line transfected with a construct in which the promoter was absent, and in a different cell line which does not express endogenous osteoactivin and which is transfected with the promoter-reporter construct.

Once a bona fide clonal osteoblastic cell line expressing the human osteoactivin promoter-reporter construct is identified, the cell line is expanded and submitted for high throughput screening to identify agents capable of modulating (e.g., increasing or decreasing) the expression of the reporter gene. When reporter expression is greater in the presence of the candidate compound than in its absence, the candidate compound is identified as a stimulator of osteoactivin expression. Alternatively, when reporter expression is less in the presence of the candidate compound than in its absence, the candidate compound is identified as an inhibitor of osteoactivin expression. The level of reporter expression can be determined by methods described herein for detecting the level of reporter osteoactivin mRNA or protein produced by the cell.

In another embodiment, the osteoactivin protein, or biologically active portion thereof, is contacted with a compound known to bind osteoactivin, e.g., an osteoactivin antibody, to form an assay mixture. The assay mixture is then contacted with a test compound, and the ability of the test compound to interact with an osteoactivin protein is determined. Determining the ability of the test compound to interact with an osteoactivin protein includes determining the ability of the test compound to preferentially bind to osteoactivin or biologically active portion thereof, or to modulate the activity of osteoactivin, as compared to the known compound.

Additionally, the invention encompasses diagnostic and prognostic assays. Accordingly, the presence, level, or absence of osteoactivin protein or nucleic acid expression in a biological sample can be evaluated by methods described herein. In one embodiment, the method comprises obtaining a biological sample from a test mammal and contacting the biological sample with a compound or an agent capable of detecting osteoactivin protein or nucleic acid (e.g., mRNA, genomic DNA) that encodes osteoactivin protein such that the presence of osteoactivin protein or nucleic acid is detected in the biological sample. The term "biological sample" includes tissues, cells and biological fluids isolated from a mammal, as well as tissues, cells and fluids present within a mammal. A preferred biological sample is serum. The level of expression of the osteoactivin gene can be measured in a number of ways including, but not limited to, measuring the mRNA encoded by the osteoactivin gene; measuring the amount of protein encoded by the osteoactivin gene; or measuring the activity of the protein encoded by the osteoactivin gene.

In another example, a control sample is contacted with a compound or agent capable of detecting osteoactivin mRNA, or genomic DNA. The presence of osteoactivin mRNA or genomic DNA in the control sample is then compared with the presence or level of osteoactivin mRNA or genomic DNA in the test sample. The control sample is obtained from a normal bone, whereas the test sample can be obtained from a site of aberrant bone growth.

A variety of methods can be used to determine the level of osteoactivin protein expressed. In general, these methods include using an agent that selectively binds to osteoactivin, such as an antibody, to evaluate the level of osteoactivin in the sample. In a preferred embodiment, the antibody bears a detectable label. Useful antibodies include any of those described above.

The detection methods can be used to detect osteoactivin protein in a biological sample in vitro as well as in vivo. In vitro techniques for detection of osteoactivin protein include enzyme linked immunosorbent assays (ELISAs), immunoprecipitations, immunofluorescence, enzyme immunoassay (EIA), radioimmunoassay (RIA), and Western blot analysis. In vivo techniques for detection of osteoactivin protein include introducing into a mammal a labeled anti-osteoactivin antibody. For example, the antibody can be labeled with a radioactive marker whose presence and location in a mammal can be detected by standard imaging techniques.

The invention is further illustrated by the following examples that should not be construed as limiting. The contents of all references, patents and published patent applications cited throughout this application are incorporated herein by reference.

EXAMPLES

Reagents

All chemicals were of molecular biology grade or higher and were purchased from Sigma (St. Louis, Mo.) unless otherwise noted. All cell culture media were purchased from Life Technologies (Gaithersburg, Md.).

Animals

An inbred colony of osteopetrotic (op) mutant rats consisting of heterozygous breeders is maintained at Temple University School of Medicine (Philadelphia, Pa.). Homozygous mutants (op/op) are distinguished from normal littermates (+/?) by radiographic analysis between 1 and 3 days after birth by the failure of the mutants to develop bone marrow cavities. Because the genotype of phenotypically normal rats cannot be distinguished, except by breeding experiments, the normal littermates used in this study were of either heterozygous (+/op) or homozygous (+/+) normal genotype. All animals were maintained and used according to the principles in the NIH Guide for the Care and Use of Laboratory Animals (1985), and guidelines established by the IACUC of Temple University.

Example 1

Primary Osteoblast Cultures

Normal diploid osteoblasts were isolated from the calvaria of 1–3 day old op/op mutant or normal littermates rats by sequential trypsin/collagenase digestion and plated in 100 mm dishes in minimum essential medium (MEM) supplemented with 10% fetal bovine serum (FBS; Gemini Bioproducts, Calabases, CA) at a density of $5 \times 10^5$ cells/dish (Owen, et al., *J. Cell. Physiol.* 143:420–430 (1990)). Media was changed every other day throughout the time course of culture and for media changes after day 6 of culture, MEMα supplemented with 50 μg/ml ascorbic acid, 2 mM inorganic phosphate, and 10% FBS was used to feed the cells.

Example 2

RNA Isolation

Total cellular RNA was isolated from calvaria and long bones (femurs and tibias) harvested from two week old op/op mutant rats and their normal littermates.

Prior to freezing, the ends of the long bones were removed at the growth plate and bone marrow was flushed from the shafts of normal bones with saline (4° C.) using a 25-gauge needle. Flushing of the bone marrow was only possible in normal rats; op mutants had no marrow cavities. Total RNA was prepared from pools of a minimum of six samples per phenotype and bone site (calvaria versus long bone). Total RNA was prepared as described by Thiede et al. (*Endocrinology* 135:929–37 (1994)). Briefly, samples were frozen in liquid nitrogen, pulverized on dry ice, and homogenized in 5 M guanidinium isothiocyanate, 72 mM β-mercaptoethanol, and 0.5% sarkosyl. Homogenates were layered over a cesium chloride (CsCl) cushion (5.7 M CsCl and 30 mM sodium acetate (NaAc)), centrifuged at 100,000×g overnight, and total RNA recovered by precipitation of the resulting pellets.

RNA was isolated from the rat osteoblast cultures, as well as from liver, spleen, thymus and brain harvested from 2, 4, and 6 week-old op rats and their normal littermates using TRIzol® (Life Technologies, Gaithersburg, Md.). The RNA concentration of each sample was quantitated by absorbance at 260 nm. The integrity and accuracy of the spectrophotometric measurement of each RNA sample was assessed by electrophoresis of 1 μg on an ethidium bromide-stained, formaldehyde-agarose minigel.

Example 3

Differential Display of mRNA

Prior to differential display, bone RNA samples were treated with DNase I (Roche Molecular Biochemicals, Indianapolis, Ind.) to eliminate any potential contamination with genomic DNA. The basic principle of mRNA differential display was first described by Liang and Pardee (1992) *Science* 257:967–971. Briefly, 0.5 μg RNA from each sample (total of 4 independent samples, mutant and normal, calvaria and long bone) was reverse transcribed using each of 12 two-base-anchored oligo-dT primers provided in the Hieroglyph mRNA profile kits (Beckman Coulter Inc., Fullerton, Calif.) to subdivide the mRNA population. First strand cDNAs were amplified by the polymerase chain reaction (PCR) for 30 cycles using one of 4 upstream arbitrary primers (also provided in the kit) and the same anchoring primers used for first strand synthesis. This resulted in 48 possible primer combinations for each kit (total of 5 kits) and each PCR amplification was run in duplicate from the same first-strand cDNA template. All amplified cDNAs were radiolabeled with $^{33}$P-dATP ([α-$^{33}$P] dATP, 2500 Ci/mmol, Amersham Pharmacia Biotech, Piscataway, N.J.). The radiolabeled PCR products were electrophoresed on 4.5% denaturing polyacrylamide gels and dried using the Genomyx LR differential display apparatus (Beckman Coulter).

As shown in FIG. 3, differential display analysis of op/op mutant versus normal calvaria and long bone RNA revealed an mRNA that was overexpressed in the op/op mutant bone RNA.

Following autoradiography, the bands were visually assessed and those representing differentially expressed cDNAs (exclusively expressed or highly overexpressed in one phenotype and confirmed in duplicate PCR amplifications) were excised from the gel. Each cDNA of interest was reamplified by PCR and used to probe a Northern blot to confirm its differential expression.

Example 4

Northern Blot Analysis

Twenty μg of total RNA from op mutant and normal bone/soft tissue or normal osteoblast cultures were electrophoresed on 1% formaldehyde-agarose gels and transferred to nylon membranes (Scheicher & Schuell, Keene, N H.). Blots were hybridized with a $^{32}$P-labeled ([α-$^{32}$P]dCTP, 6000 Ci/mmol, Amersham Pharmacia Biotech, Piscataway, N.J.) full length rat osteoactivin cDNA probe (Rediprime™II, Amersham Pharmacia Biotech) using methods described in Thiede et al., *Endocrinology* 135:929–37 (1994). Blots were then autoradiographed, stripped and re-probed with an 18s rRNA probe used as a control to normalize for differences in loading and transfer.

FIG. 4A shows that the osteoactivin mRNA expression levels were 5–7 times higher in the op mutant (M) calvaria as compared to the normal (N) calvaria. cDNAs which were confirmed to be differentially expressed by Northern blot analysis were cloned into PCR-Script (Stratagene, Lajolla, Calif.), miniprep DNA was prepared, and plasmids with the appropriately sized inserts were sequenced.

Example 5

Cloning of Rat Osteoactivin cDNA

Approximately 600 bp of sequence corresponding to the 3' end of rat osteoactivin was obtained from the differential display clone. This fragment was used as a probe to screen a rat kidney cDNA library by conventional means. A single clone was identified after three rounds of screening and DNA sequence analysis showed that it contained an open reading frame of 1719 bp as depicted in FIG. 1A. Following confirmation by Northern blot analysis (see FIGS. 4A and 4B), this clone was sequenced and found to be related to a human sequence (nmb) of unknown function. This cDNA and predicted protein was named osteoactivin to reflect its potential role in osteoblast function. Cloning of the entire coding region of osteoactivin nucleic acid sequence revealed an open reading frame capable of encoding a protein of 572 amino acids with 70% identity to human nmb as depicted in FIG. 2B. Osteoactivin has a predicted molecular weight of 63.8 kD. Hydropathy analysis, as provided in FIG. 1B revealed a potential leader sequence and several potential transmembrane spanning domains throughout the protein, suggesting membrane association.

Example 6

DNA Sequencing

DNA was sequenced using standard dideoxy methodologies. Gaps and ambiguities in the sequence were handled by direct sequencing of required regions using specific primers. The nucleic acid sequence of rat osteoactivin has been deposited in GenBank under Accession Number AF184983.

In FIGS. 2A and 2B, the nucleotide (SEQ ID NOS: 1, 7, and 8) and predicted amino acid sequences (SEQ ID NOS: 2, 5, and 6) respectively, of rat osteoactivin and human and mouse nmb were compared. FIG. 2A reveals that there is a 76% sequence identity in the nucleotide sequences between rat and human. The predicted protein sequence of rat osteoactivin has a proline seine-rich 14 amino acid insertion beginning at residue 333 that is not present in the human nmb protein sequence, as shown in FIG. 2B. On the protein level, the sequences of rat osteoactivn and human nmb are 69% identical.

Example 7

Antibody Preparation

Peptide 35 H-CPDHMRENNQLRGWSSDE-NH$_2$ (SEQ ID NO:3) and peptide 551 H-KAPFSRGDREKDPLLQDKC-NH$_2$ (SEQ ID NO:4) were conjugated to Keyhole Limpet Hemocyanin (KLH) by Cys residues added at N-terminal end of peptide 35 of the osteoactivin protein (SEQ ID NO:2) or at C-terminal end of peptide 551. For each peptide, two chickens were immunized with 100 μg/chicken/Freunds complete adjuvant on the following immunization schedule: Day 1, pre-immune eggs collected, first boost; Day 14, $2^{nd}$ boost; Day 28, $3^{rd}$ boost; Day 42, $4^{th}$ boost; and Day 49, begin collecting eggs. Twelve eggs were collected and pooled from each chicken. Affinity purified peptide-specific immune IgY was purified by affinity chromatography using peptide immobilized on column. (Hanlos and Lane, supra).

Example 8

Immunolocalization of Osteoactivin in Primary Rat Osteoblasts

Primary osteoblasts isolated from newborn normal rat calvaria were plated in 100 mm dishes at a density of $5 \times 10^5$ cells/dish in Earl's medium supplemented with 10% fetal bovine serum (FBS), 50 µg/ml ascorbic acid, and 10 mM β-glycerolphosphate and cultured for 1 week. Cells were fixed in 4% paraformaldehyde for 10 minutes at 4° C., treated with 0.1% Triton X-100 for 10 minutes at room temperature (RT), and then blocked with 10% goat serum for 15 minutes at RT. They were then stained with an anti-osteoactivin polyclonal antibody raised in chickens against amino acid residues 551–558 at the C-terminal end of the osteoactivin protein or with buffer alone at a dilution of 1:50 in phosphate buffered saline (PBS) and incubated overnight at 4° C. Following three washes in PBS (5 minutes each), Cy3 conjugated goat anti-chicken secondary antibody (Jackson Immuno Research, West Grove, Pa.), which served as a fluorescent marker, was added (1:1000 in PBS) and incubated for 1 hr at RT. Osteoactivin was visualized by fluorescence microscopy (FIG. 5).

In another experiment to further study the properties of the protein, immunofluorescent staining was performed on primary rat osteoblasts cultured in chamber slides for 5 days following plating at a density of 12,400 cells per chamber. The cells were fixed in 4% paraformaldehyde and were stained overnight at 4° C. using 1 µg/ml polyclonal osteoactivin antibody (Cambridge Research Biochemicals, Billingham, Cleveland, UK) as the primary antibody. The antibody was raised in chickens against amino acid residues 551–568 at the C-terminal end of the rat osteoactivin protein. More specifically, the polyclonal antibody was made against the following peptide conjugated to keyhole limpet hemocyanin: H-KAPFSRGDREKDPLLQDKC-NH$_2$. The primary antibody was then detected following washing by incubation with a 1:10,000 dilution of a Cy3-conjugated donkey anti-chicken secondary antibody (Jackson ImmunoResearch, West Grove, Pa.) for 1 hr at room temperature. The results are shown in FIG. 5A, which indicates immunofluorescent staining in the perinuclear region of the cell.

For co-localization within the RER, cells were stained with the cell permanent, fluorescent probe DiOC$_5$, a membrane marker for RER (Molecular Probes, Eugene, Oreg.) following incubation with the primary and secondary antibodies. The results, shown in FIG. 5B and the overlay of FIGS. 5A and 5B in FIG. 5C, indicate that osteoactivin co-localizes in the RER in primary rat osteoblasts, suggesting that osteoactivin is a secreted protein.

Example 9

Northern Blot Analysis of Osteoactivin Expression in Calvaria and Long Bone of Rats of Different Ages Twenty µg of total RNA isolated from normal (N) or mutant (M) calvaria or long bones at 2, 4, and 6 weeks of age was electrophoresed in a 1% agarose formaldehyde gel, blotted, and probed for osteoactivin, as described in Example 4 above. Northern analysis was repeated three times using independent RNA samples with similar results.

Figure 6:
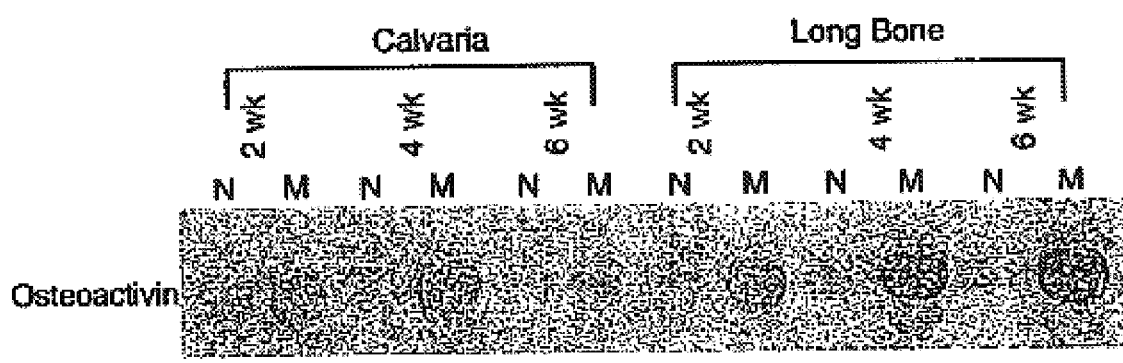
FIG. 6 is a representation of a Northern blot of osteoactivin expression in calvaria and long bone of mutant (M) and normal (N) rats 2 weeks (2 wk), 4 weeks (4 wk) and 6 weeks (6 wk) old. Osteoactivin was expressed at higher levels in the mutant bones at all ages examined, and appeared to decrease with age in the normal rats, while in the mutants expression remained high, especially in the long bone RNA.

As shown in FIG. 6, osteoactivin expression was higher in mutant calvaria and long bones when compared to normal bones at all ages examined. In normal animals, osteoactivin expression decreases with age in both calvaria and long bones. However, in the mutants, osteoactivin expression is still detectable in the calvaria at six weeks of age and, in long bones, is highly expressed at all ages examined.

Example 10

Northern Blot Analysis of Osteoactivin Expression in Primary Rat Osteoblast Cultures Total RNA was isolated from normal (N) or mutant (M) osteoblast cultures at 1, 2 and 3 weeks of culture. Twenty µg of RNA from each sample was subjected to Northern blot analysis, as described in Example 4 above.

Figure 7A:
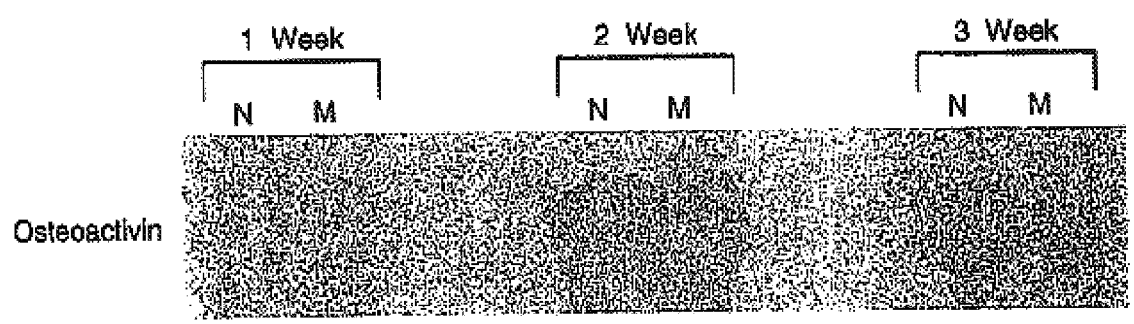
FIG. 7A is a representation of a Northern blot showing osteoactivin expression in primary rat osteoblast cells derived from normal (N) or mutant (M) calvaria cultured for 1 week, 2 weeks, or 3 weeks.
Figure 7B:
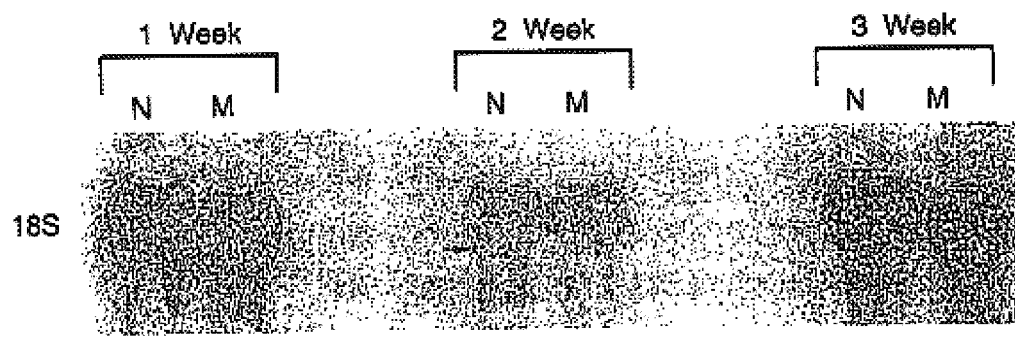
FIG. 7B is a representation of the same Northern blot in FIG. 7A which was stripped and reprobed with a probe for 18S rRNA.

As shown in FIG. 7A, the temporal pattern demonstrated a remarkable increase in expression between 1 week (proliferation stage) and 2 weeks (matrix maturation stage), with a modest decrease at 3 weeks in culture (mineralization stage). There was no significant difference between osteoblast cultures derived from normal or mutant calvaria. The blot was stripped and reprobed for 18s rRNA to normalize for differences in loading and/or blotting (FIG. 7B). Similar results were obtained from two separate experiments.

Example 11

Detection of Secreted Osteoactivin Protein in Osteoblast Culture Conditioned Media Osteoblast cultures were established from the calvaria of newborn op/op mutant rats or their normal littermates by established methods and plated at a density of 500,000 cells per 100 mm dish in MEMA supplemented with 10% FBS. Cell culture media was changed every other day. Six days after the initiation of the cultures, the cells were washed twice with culture media lacking FBS. 10 ml of serum free culture medium was then added per 100 mm dish and the cells were cultured for an additional 24 hours. This medium was then harvested and the proteins concentrated using a 10 kD molecular weight cut-off concentrator (Millipore, Bedford, Mass.). The concentration of protein in these concentrated samples was determined by the method of Bradford (*Analyst. Biochem.* 72:246–54 (1976)) using reagents from Pierce (Rockford, Ill.). 10 µg of concentrated protein from the op/op mutant or normal osteoblast cultures was electrophoresed in a 10% polyacrylamide-sodium dodecyl sulfate (SDS) gel and then transferred to polyvinylidene fluoride (PVDF) membrane by electroblotting. This blot was blocked for 1 hour at room temperature in 10% non-fat milk in phosphate buffered saline (PBS)-0.2% Tween 20 (PBS-Tween) and then incubated overnight at 4° C. in blocking solution containing 0.325 µg/ml chicken anti-rat osteoactivin 551 antibody. Following four washes in PBS-Tween, the blot was incubated at RT for 1 hour in blocking solution containing a 1:5000 dilution of horseradish peroxidase conjugated donkey anti-chicken antibody (Jackson Immunoresearch, West Grove, Pa.). Following four washes in PBS-Tween, the blot was developed using Enhanced Chemiluminescence (ECL) reagents (Amersham Pharmacia Biotech, Piscataway, N.J.) and visualized by exposure to film.

Figure 8:
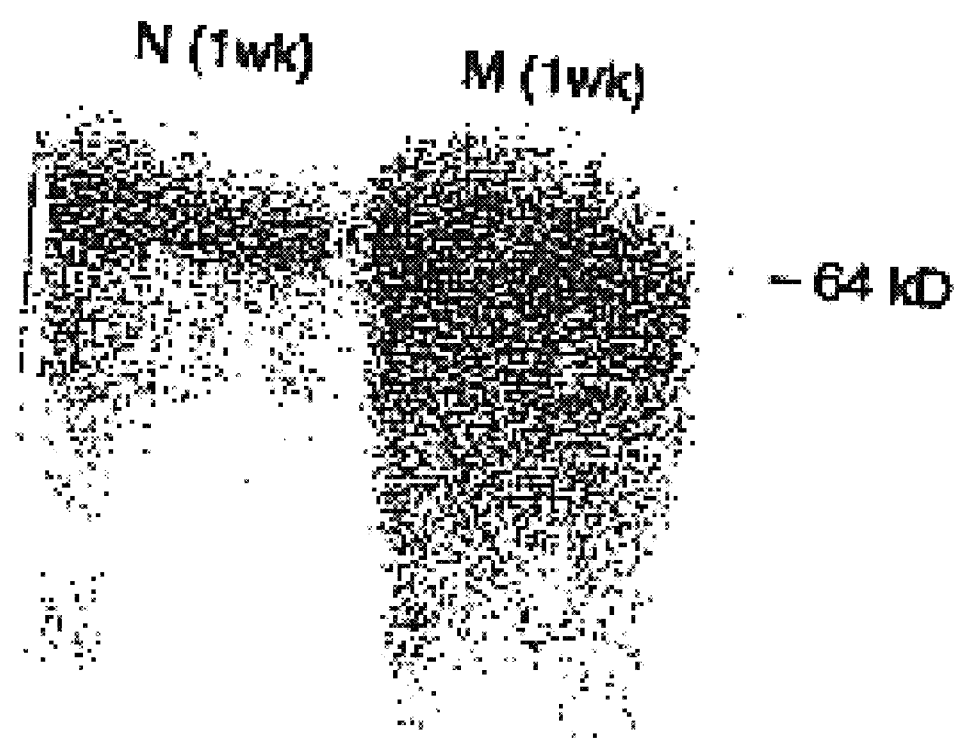
FIG. 8 is a representation of a Western blot showing secreted osteoactivin protein from osteoblasts isolated and cultured for one week from either mutant (M) or normal (N) rat calvaria and probed with a chicken anti-rat osteoactivin antibody raised against peptide 551 (SEQ ID NO:4).

The results shown in FIG. 8 demonstrate that one week old mutant osteoblast cultures secrete significantly more osteoactivin protein than normal osteoblast cultures.

Example 12

Detection of Osteoactivin Protein in the Tibia of Normal and op/op Mutant Rats

Figure 9:
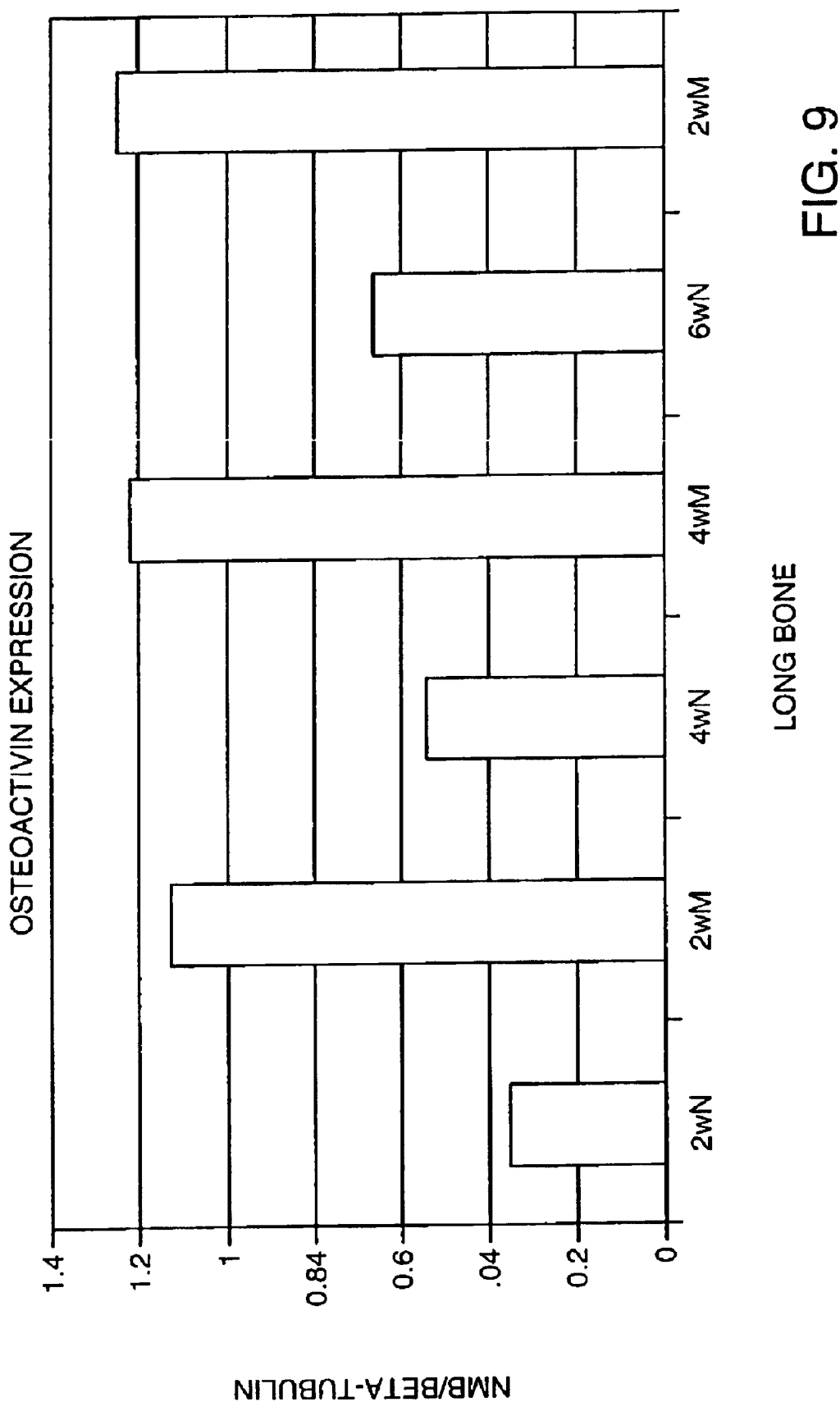
FIG. 9 is a graphic representation of the quantitation of a Western blot of osteoactivin expression (normalized as to β-tubulin as a control for protein loading and blotting efficiency) in long bones from 2 week (2 wk), 4 week (4 wk), and 6 week (6 wk) old mutant (M) or normal (N) rats.

Tibia were harvested from op/op mutant rats or from their normal littermates at the indicated weeks of age, immediately frozen in liquid nitrogen, and stored at −80° C. until all samples were collected. The frozen bones were then homogenized in RIPA buffer (50 mM Tris pH 7.5, 150 mM NaCl, 1.0% NP-40, 0.1% SDS, 0.5% sodium deoxycholate; *Molecular Cloning: A Laboratory Manual*, Cold Spring Harbor Press (1989), 18.38) containing protease inhibitors (Complete tablets, Roche Molecular Biochemicals, Indianapolis, Ind.), and the insoluble material removed by centrifugation. The concentration of soluble proteins was determined by the method of Bradford (*Analyst. Biochem.* 72:246–54 (1976)) using reagents from Pierce (Rockford, Ill.). 40 μg of protein from the op/op mutant or normal tibia was electrophoresed in a 10% polyacrylamide-SDS gel and then transferred to PVDF membranes by electroblotting. This blot blocked for 1 hr at room temperature in 10% non-fat milk in PBS-Tween and then incubated overnight 4° C. in blocking solution containing 0.325 μg/ml chicken anti-rat osteoactivin 551 antibody. Following four washes in PBS-Tween, the blot was incubated at RT for 1 hour in blocking solution containing a 1:5000 dilution of horseradish peroxidase conjugated donkey anti-chicken antibody (Jackson Inmmunoresearch, West Grove, Pa.). Following four washes in PBS-Tween, the blot was developed using ECL reagents (Pierce (Rockford, Ill.) and visualized by exposure to film. The blot was then stripped of the antibodies and detection reagents and blocked as described. The blot was incubated overnight at 4° C. in blocking solution containing 0.75 μg/ml mouse anti-rat tubulin antibody as a control for protein loading between the samples and for the efficiency of blotting across the gel. Following four washes in PBS-Tween, the blot was incubated at RT for 1 hour in blocking solution containing a 1:5000 dilution of horseradish peroxidase conjugated donkey anti-rabbit antibody (Jackson Immunoresearch, West Grove, Pa.), washed, developed, and visualized as described above. The film images from the osteoactivin and β-tubulin experiments were quantitated by scanning densitometry and the data were expressed as a ratio of the osteoactivin to β-tubulin signal in each sample (FIG. 9).

These results show that the expression of osteoactivin protein was significantly higher in mutant versus normal rat tibia in all ages examined.

Example 13

Inhibition of Osteoblast Differentiation Following Treatment with Antibodies against Osteoactivin Osteoblast cultures were established from the calvaria of newborn op/op mutant rats or their normal littermates by established methods and plated at a density of 14,200 cells per well of a 24-well plate in MEMA supplemented with 10% fetal bovine serum. Cell culture media was changed every other day and, beginning at day 6 of culture, cells were fed with differentiation medium (MEMA supplemented with 10% FBS, 50 μg/ml ascorbic acid, 10 mM β-glycerophosphate). Beginning at the media change on day 2 of culture and for every subsequent media change, affinity purified antibodies to rat osteoactivin (antibody 551) or control non-immune IgY antibodies were added to the fresh culture medium final concentrations of 4, 20, or 40 μg/ml. All cultures were terminated at 21 days and analyzed for calcium deposition in the cell/matrix layer using a colorimetric kit from Sigma.

Figure 10:
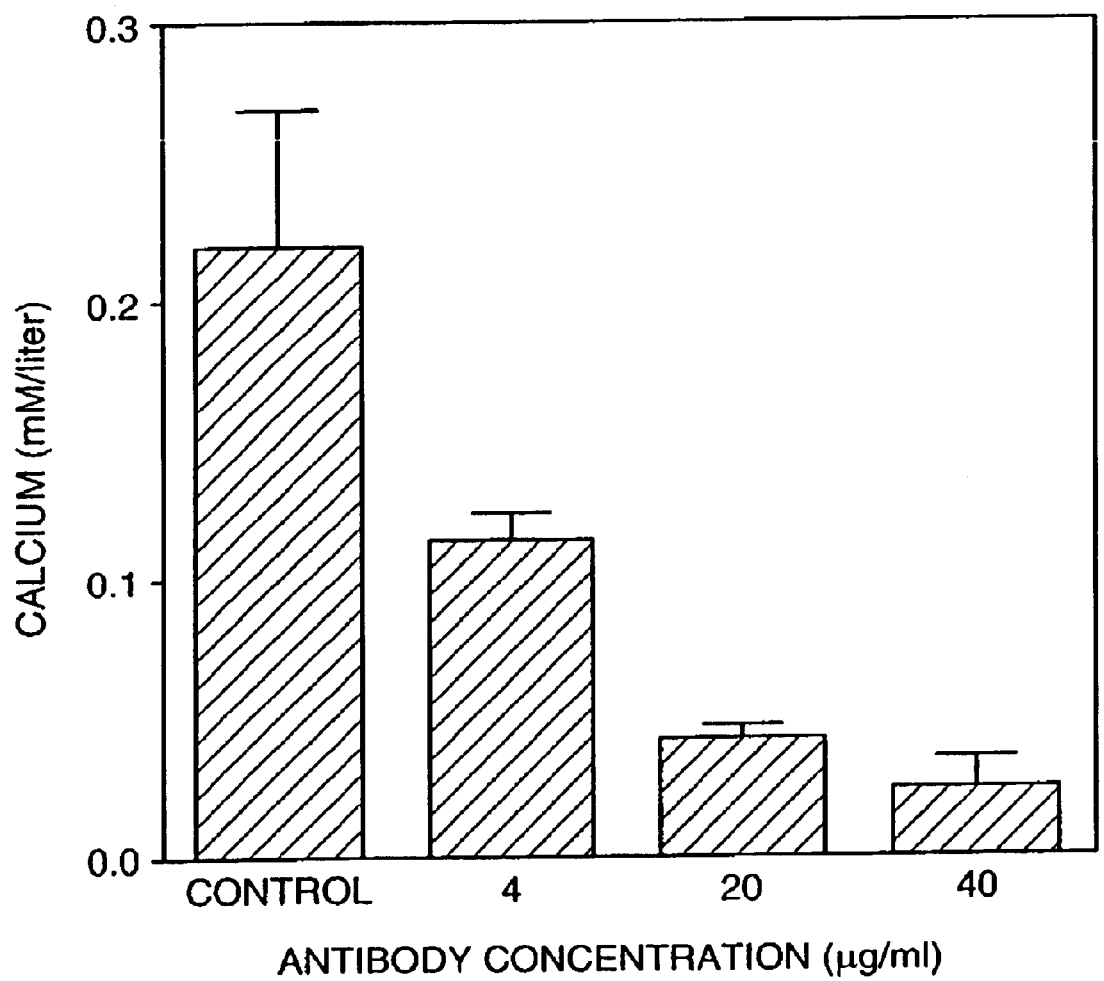
FIG. 10 is a graphic representation of the ability of anti-osteoactivin antibodies to inhibit osteoblast differentiation as measured by calcium deposition.

These data (FIG. 10) indicate that the antibodies to osteoactivin inhibit rat osteoblast differentiation in vitro (as measured by calcium deposition) in a dose dependent manner.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. An isolated nucleic acid molecule, wherein said nucleic acid molecule encodes a polypeptide comprising SEQ ID NO: 2.

2. The nucleic acid molecule of claim 1, wherein said nucleic acid comprises the nucleic acid sequence of nucleotides 115–1,830 of SEQ ID NO: 1.

3. An isolated nucleic acid molecule, wherein said nucleic acid molecule encodes a polypeptide comprising amino acids 23–572 of SEQ ID NO: 2.

4. A biologically functional expression vector comprising a nucleic acid sequence encoding an osteoactivin protein, wherein said osteoactivin protein:

(a) comprises the amino acid sequence of SEQ ID NO: 2, or (b) comprises amino acids 23–572 of SEQ ID NO: 2.

5. A method for producing a substantially pure osteoactivin protein, or polypeptide fragment thereof, comprising:

(a) culturing a cell stably transformed with the nucleic acid molecule of claim 1 encoding an osteoactivin protein; and (b) isolating and purifying said ostecactivin protein from said culture medium.

6. A method for producing a substantially pure osteoactivin protein, or polypeptide fragment thereof, comprising:

(a) culturing a cell stably transformed with the nucleic acid molecule of claim 2 encoding an osteoactivin protein; and (b) isolating and purifying said osteoactivin protein from said culture medium.

7. A method for producing a substantially pure osteoactivin protein, or polypeptide fragment thereof comprising:

(a) culturing a cell stably transformed with the nucleic acid molecule of claim 3 encoding an osteoactivin protein; and (b) isolating and purifying said osteoactivin protein from said culture medium.

8. A host cell comprising the nucleic acid molecule of claim 1.

9. The host cell of claim 8, wherein the nucleic acid molecule is operably linked to a regulatory region.

10. A host cell comprising the nucleic acid molecule of claim 2.

11. The host cell of claim 10, wherein the nucleic acid molecule is operably linked to a regulatory region.

12. A host cell comprising the nucleic acid molecule of claim 3.

13. The host cell of claim 12, wherein the nucleic acid molecule is operably linked to regulatory region.

* * * * *